United States Patent
Marti

(10) Patent No.: US 8,329,919 B2
(45) Date of Patent: *Dec. 11, 2012

(54) SALT HYDRATES

(75) Inventor: Erwin E Marti, Basel (CH)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/247,281

(22) Filed: Sep. 28, 2011

(65) Prior Publication Data

US 2012/0022268 A1  Jan. 26, 2012

Related U.S. Application Data

(62) Division of application No. 11/013,111, filed on Dec. 15, 2004, now Pat. No. 8,058,301, which is a division of application No. 10/353,389, filed on Jan. 29, 2003, now Pat. No. 6,869,970.

(60) Provisional application No. 60/354,199, filed on Feb. 4, 2002.

(51) Int. Cl.
C07D 257/00 (2006.01)
A01N 43/64 (2006.01)

(52) U.S. Cl. ........................... 548/253; 514/381

(58) Field of Classification Search ................ None
See application file for complete search history.

(56) References Cited

U.S. PATENT DOCUMENTS

| | | | |
|---|---|---|---|
| 5,399,578 A | 3/1995 | Bühlmayer et al. | 514/381 |
| 5,877,193 A | 3/1999 | Cesura et al. | 514/370 |
| 6,869,970 B2 | 3/2005 | Marti | 514/381 |
| 2002/0132839 A1* | 9/2002 | Ganter et al. | 514/381 |

FOREIGN PATENT DOCUMENTS

| | | |
|---|---|---|
| CA | 2196425 A1 | 12/1996 |
| WO | WO 9631234 A1 | 10/1996 |
| WO | WO 01/80857 | 11/2001 |
| WO | WO 02/06253 A1 | 1/2002 |
| WO | WO 0206253 A1 | 1/2002 |

OTHER PUBLICATIONS

Suzuki et al., "First Systermatic Chiral Syntheses of two Pairs of Enantiomers with 3,5-Dihydroxyheptenoic Acid Chain, associated with a Potent Synthetic Statin NK-104" Bioorganic & Medicinal Chemistry Letters, No. 9, pp. 2977-2982 (1999).
Nicholas D. Cheronis, 1958, "Semimicro Experimental organic chemistry", chapter 5.
Saleki-Gerhardt A et al, "Hydration and Dehydration of Crystalline and Amorphous Forms of Raffinose", J Pharm Sciences, vol. 84(3), pp. 318-323 (1995).
Sathe R et al, "Dehydration and Hydration Kinetics, Phase Change, Colubility and Dissolution Behavior of Fenoprofen Calcium", Drug Development and Industry Pharmacy, vol. 21, No. 16, pp. 1887-1894 (1995).
Pharmaceutical Sciences, Nanzando Co., Ltd., 1st edition, p. 28 (Mar. 20, 1989) [*Note: this reference is currently not available due to earthquake in Japan*].
Gancy Alan B, "Preparation and characterisation of the nonahydrate and pentahydrate of aluminum sulfate", Thermochimica Acta, vol. 54, No. 1 / 2, pp. 105-114 (1982).
New Experimental Science 8, Synthesis of Inorganic Compound II, Maruzen, Section of Uranium (VI) Oxide Hydrate, 2nd edition, pp. 728-729 (Aug. 20, 1979).
Cheronis publication, "Semimicro Experimental Organic Chemistry", 1958, chapter 5.

* cited by examiner

*Primary Examiner* — Michael G Hartley
*Assistant Examiner* — Nabila Ebrahim
(74) *Attorney, Agent, or Firm* — Joseph T. Majka

(57) ABSTRACT

The invention relates to new forms of salts of valsartan or crystalline, also partly crystalline and amorphous salts of valsartan, the respective production and usage, and pharmaceutical preparations containing such a salt.

1 Claim, No Drawings

SALT HYDRATES

This application is a Divisional application of Ser. No. 11/013,111, filed Dec. 15, 2004, now allowed, which is a Divisional application of Ser. No. 10/353,389, filed Jan. 29, 2003 now issued as U.S. Pat. No. 6,869,970 on Mar. 22, 2005, which claim benefit of Provisional Application Ser. No. 60/354,199, filed Feb. 4, 2002, now abandoned.

The invention relates to additional new salts and salt hydrates of the $AT_1$ receptor antagonist (S)—N-(1-carboxy-2-methyl-prop-1-yl)-N-pentanoyl-N-[2'-(1H-tetrazol-5-yl)-biphenyl-4-yl-methyl]-amine (valsartan) of formula

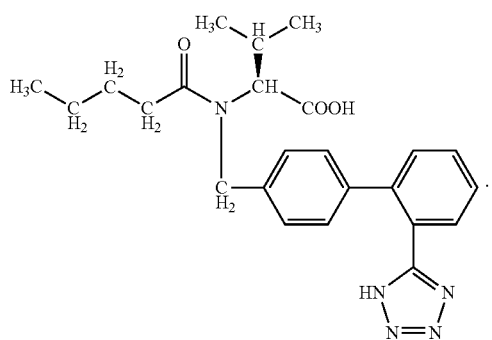

(I)

The active ingredient valsartan is the free acid which is described specifically in EP 0443983, especially in example 16; it has two acidic hydrogen atoms: (i) the hydrogen atom (H atom) of the carboxyl group, and (ii) that of the tetrazole ring. Accordingly, one acidic H atom (primarily the carboxyl H atom) or both acidic H atoms may be replaced by a monovalent or higher valent, e.g. divalent, cation. Mixed salts may also be formed.

EP 443983 does not disclose any specific salts or salt solvates, e.g. hydrates, of valsartan. Also, it does not mention any special properties of salts or salt solvates, e.g. hydrates. Meanwhile, the active ingredient valsartan has been introduced as an anti-hypertensive agent in a series of countries under the trade name DIOVAN.

The free acid valsartan has a melting point in a closed crucible of 80 to 95° C. and in an open crucible of 105 to 110° C. and a melting enthalpy of 12 kJ/mol. The specific optical rotation is $[\square]^{20}_D=(-70\pm2)°$ measured for a concentration of c=1% in methanol.

The density of the valsartan crystals and of the salt hydrates was determined by a helium pycnometer (Accupyc 1330 of Micromeritics, Norcross, Ga., USA). The density for the crystals of the free acid valsartan is 1.20±0.02.

The X-ray diffraction diagram consists essentially of a very broad, diffuse X-ray reflection; the free acid is therefore characterised as almost amorphous under X-ray. The melting point linked with the measured melting enthalpy of 12 kJ/mol unequivocally confirms the existence of a considerable residual arrangement in the particles or structural domains for the free acid valsartan.

There is a need for more stable, e.g. crystalline forms of valsartan, which, for example, are even easier to manage in the drying or grinding processes following the final stage of the chemical preparation process, and also in the steps for preparing the pharmaceutical formulations and lead to an improvement of the process for the manufacture of the drug substance. Many futile attempts have been made to find improved forms through salt formation, the forms ideally being as crystalline as possible, as well as physically and chemically stable. Only the salts according to the present invention including both of the substances assigned here as starting materials, there solvates, e.g. hydrates and polymorphous forms thereof exhibit the desired improved properties.

The formation of salts and salt hydrates of valsartan with the desired advantageous properties has proved to be difficult. In the majority of cases, for example, amorphous salts with little stability are obtained (such as hard foams, waxes or oils). Extensive research has shown that the additional salts and salt hydrates of valsartan according to the invention have proved to be particularly advantageous compared with the free acid valsartan.

The objects of the present invention are salts and salt hydrates of valsartan which are selected from the group of earth alkalimetals consisting of the magnesium salt and the calcium salt, as well as salt mixtures, or respectively, an amorphous form, a solvate, especially hydrate, as well as a polymorphous form thereof, the respective production and use, and pharmaceutical preparations containing such salts.

Salt mixtures are (i) single salt forms from different cations selected from the above group or (ii) mixtures of those single salt forms which exist for example in the form of conglomerates or (III) mixtures of a single salt or a salt hydrate consisting of different physical phases such as several polymorphic forms, of different hydrates or also the anhydrate, of different amorphous forms or (IV) mixtures of any form listed under (I), (II), and (III) with each other.

Preferred salts are for example selected from the
calcium salt of valsartan in crystalline and amorphous forms, especially in hydrate form, primarily the tetrahydrates, the trihydrates, the monohydrate, the di-(calcium salt of valsartan) pentahydrate, the anhydrate, the amorphous forms thereof;
magnesium salt of valsartan in crystalline form, especially in hydrate form, primarily the hexahydrates, the trihydrates, the monohydrate, the anhydrate, the amorphous forms thereof.

The salts according to the invention preferably exist in isolated and essentially pure form, for example in a degree of chemical purity of >95%, preferably >98%, primarily >99%. The enantiomer purity of the salts according to the invention is >98%, preferably >99%.

Compared with the free acid, the salts according to the invention, or the amorphous forms, solvates such as salt hydrates, and also the corresponding polymorphous forms thereof, have unexpectedly advantageous properties. Under given conditions, the crystalline salts and crystalline salt hydrates have a clear melting point which is linked with a marked, endothermic melting enthalpy. The crystalline salts, salt hydrates, amorphous forms and mixtures thereof according to the invention have limited stability, i.e. as the solid, they have a restricted stability range. To be stabilised, they require certain measures which can be achieved for example by galenic formulations.

In addition, both the crystalline and the amorphous salts and salt hydrates according to the invention have a high degree of dissociation in water and thus substantially improved water solubility. These properties are of advantage, since on the one hand the dissolving process is quicker and on the other hand a smaller amount of water is required for such solutions. Furthermore, the higher water solubility can, under certain conditions, also lead to increased biological availability of the salts or salt hydrates in the case of solid dosage forms. Improved properties are beneficial especially to the patients.

The high crystallinity of certain salt hydrates allows the use of a choice of analytical methods, especially the various X-ray methods and/or the infrared spectrum preferably by means of ATR-IR (Attenuated Total Reflection-Infrared Spectroscopy), the usage of both methods permit a clear and simple analysis of their release to be made. This factor is also of great importance to the quality of the active substance and its galenic forms during production, storage and administration to the patients.

The invention accordingly relates to crystalline, also partly crystalline and amorphous salts or salt hydrates of valsartan.

As well as the solvates, such as hydrates, the invention also relates to polymorphous forms of the salts according to the invention.

Solvates and also hydrates of the salts according to the invention may be present, for example, as mono-, di-, tri-, tetra-, penta-, hexa-solvates or hydrates, respectively. Solvates and hydrates may also be consisting in stoichiometric ratios for example, with two, three, four salt molecules per solvate or per hydrate molecule. Another possibility for example, that two salt molecules are stoichiometric related to three, five, seven solvent or hydrate molecules. Solvents used for crystallisation, such as alcohols, especially methanol, ethanol, aldehydes, ketones, especially acetone, esters, e.g. ethyl acetate, may be embedded in the crystal grating. Preferred are pharmaceutically acceptable solvents. The extent to which a selected solvent or water leads to a solvate or hydrate in crystallisation and in the subsequent process steps or leads directly to the free acid is generally unpredictable and depends on the combinations of process conditions and the various interactions between valsartan and the selected solvent, especially water. The respective stability of the resulting crystalline or amorphous solids in the form of salts, salt solvates or salt hydrates, must be determined by experimentation. It is thus not possible to focus solely on the chemical composition and the stoichiometric ratio of the molecules in the resulting solid, since under these circumstances both differing crystalline solids and differing amorphous substances may be produced.

The description salt hydrates for corresponding hydrates may be preferred, as water molecules in the crystal structure are bound by strong intermolecular forces and thereby represent an essential element of structure formation of these crystals which, in part, are extraordinarily stable. However, water molecules are also existing in certain crystal lattices which are bound by rather weak intermolecular forces. Such water molecules are more or less integrated in the crystal structure forming, but to a lower energetic effect. The water content in amorphous solids can, in general, be clearly determined, as in crystalline hydrates, but is heavily dependent on the drying and ambient conditions. In contrast, in the case of stable hydrates, there are clear stoichiometric ratios between the pharmaceutical active substance and the water. In many cases these ratios do not fulfil completely the stoichiometric value, normally it is approached by lower values compared to theory because of imperfection or of certain crystal defects. The ratio of organic molecules to water molecules for the weaker bound water may vary to a considerable extend, for example, even extending from the anhydrous form over mono-, di-, tri- or tetra-hydrates. On the other hand, in amorphous solids, the molecular structure classification of water is not stoichiometric; the classification may however also be stoichiometric only by chance.

In some cases, it is not possible to classify the exact stoichiometry of the water molecules, since layer structures form, e.g. in the alkali metal salts, especially in the potassium salt, so that the embedded water molecules cannot be determined in defined form.

For the crystalline solids having identical chemical composition, the different resulting crystal gratings are summarised by the term polymorphism.

Any reference hereinbefore and hereinafter, to the salts according to the invention is to be understood as referring also to the corresponding solvates, such as hydrates, and polymorphous modifications, and also amorphous forms, as appropriate and expedient.

The particularly preferred salt hydrate is the tetrahydrate of the calcium salt of valsartan in the polymorphic form $A_{1,Ca}$. In a closed specimen container, for a heating rate of $T_r=10$ K·min$^{-1}$ it has a melting point of 190±1.5° C. and a melting enthalpy of 79±4 kJ·Mol$^{-1}$. The tetrahydrate of the calcium salt of valsartan $A_{1,Ca}$ is not stable at the melting point both in respect of the hydrate water and therefore in respect of the chemical and physical structure of the molecule. The indicated melting point is a hydrate melting point which can only be measured in a closed specimen container. Gold containers with a wall thickness of 0.2 mm were used; after weighing in samples of between 2 and 4 mg salt hydrate, they were sealed by cold welding. These gold containers have an internal free volume of ca. 22 microliters. The amounts of the sample and the volume of the pressurised containers must be suitably adapted, so that strong dehydration of the salt hydrates cannot take place during measurement of the melting point. The partial pressure of the water at 191° Celsius is ca. 13 bar, so that with an open container in DSC (Differential Scanning calorimeter) during measurement of the melting point, conversion to the anhydrate takes place. Both the high hydrate melting point and the amount of the melting enthalpy are an expression of the exceptional stability of the crystal lattice of the form $A_{1,Ca}$ of the tetrahydrate of the calcium salt of valsartan. These two thermodynamic characteristics illustrate the advantageous physical properties, compared to the free acid, with the two corresponding data, namely a melting point in the closed system of 90° C. and a melting enthalpy of 12 kJ·Mol$^{-1}$. These thermodynamic data, together with the X-ray data, prove the high stability of this crystal lattice. They are the base for the special physical and chemical resistance of the tetrahydrate of the calcium salt of valsartan of the polymorphic form $A_{1,Ca}$.

Measurement of the infrared spectrum likewise took place by means of ATR-IR (Attenuated. Total Reflection-Infrared Spectroscopy) using the instrument Spektrum BX from Perkin-Elmer Corp., Beaconsfield, Bucks, England.

The tetrahydrate of the calcium salt of valsartan $A_{1,Ca}$ has the following absorption bands expressed in reciprocal wave numbers (cm$^{-1}$):
3594 (w); 3307 (w); 3056 (w); 2960 (m); 2871 (w); 1621 (st); 1578 (st); 1459 (m); 1442 (m); 1417 (m); 1407 (m); 1364 (m); 1357 (m); 1319 (m); 1274 (m); 1242 (w); 1211 (m); 1180 (m); 1149 (w); 1137 (m); 1105 (m); 1099 (m); 1012 (m); 1003 (m); 974 (m); 965 (w); 955 (w); 941 (w); 863 (w); 856 (w); 844 (m); 823 (m); 791 (m); 784 (m); 758 (m); 738 (st); 698 (m).

The intensities of the absorption bands are indicated as follows: (w)=weak; (m)=medium and (st)=strong intensity.

The characteristic absorption bands of the ATR-IR spectroscopy for the polymorphic form $A_{1,Ca}$ of the tetrahydrate of the calcium salt of valsartan are shown by the following values expressed in reciprocal wave numbers (cm$^{-1}$): 3307 (w); 2960 (m); 1621 (st); 1578 (st); 1459 (m); 1442 (m); 1417 (m); 1407 (m); 1364 (m); 1357 (m); 1319 (m); 1274 (m); 1211 (m); 1180 (m); 1137 (m); 1012 (m); 1003 (m); 974 (m); 758 (m); 738 (st); 698 (m).

The error margin for all absorption bands of ATR-IR is ±3 cm$^{-1}$.

The water content is in theory 13.2% for the tetrahydrate of the calcium salt of valsartan. Using the thermobalance TGS-2 (Perkin-Elmer Corp., Norwalk, Conn. USA) the water content was determined for the polymorphic form $A_{1,Ca}$ between 25° C. and 225° C. as 12.3%. A total formula was calculated from this $(C_{24}H_{27}N_5O_3)^{2-}Ca^{2+} \cdot (3.7\pm 0.2)H_2O$.

Using thermogravimetry, in a water-free $N_2$ atmosphere, the weight loss, i.e. the water loss for the tetrahydrate of the calcium salt of valsartan $A_{1,Ca}$ as a function of temperature, was measured at a heating rate of 10 K·min$^{-1}$. The results are illustrated in table 1.

TABLE 1

| temperature [° C.] | weight loss or water loss in % |
|---|---|
| 25 | 1.1 ± 0.5 |
| 50 | 3.3 ± 0.5 |
| 75 | 5.1 ± 0.5 |
| 100 | 9.6 ± 1.0 |
| 125 | 12.2 ± 0.5 |
| 150 | 12.9 ± 0.5 |
| 175 | 13.2 ± 0.5 |
| 200 | 13.3 ± 0.5 |
| 225 | 13.4 ± 0.5 |
| 250 | 13.3 ± 0.5 |
| 275 | 13.7 ± 0.5 |

An essential feature for the quality of a pure active substance both for the physical-chemical procedures such as drying, sieving, grinding, and in the galenic processes which are carried out with pharmaceutical excipients, namely in mixing processes, in granulation, in spray-drying, in tabletting, is the water absorption or water loss of this active substance depending on temperature and the relative humidity of the environment in question. With certain formulations, free and bound water is without doubt introduced with excipients and/or water is added to the process mass for reasons associated with the respective formulation process. In this way, the pharmaceutical active substance is exposed during the production and galenic processes over time periods of up to several hours or even days to free water of different activity (partial vapour pressure) which is mainly depending on temperature. However, it is easily possible to reach a well-defined hydrate form in the production of the active substance as well as in the formulation of a salt of valsartan after a certain equilibration time under rather constant conditions in respect to temperature and to the relative humidity.

Further characterisation of the tetrahydrate of the calcium salt of valsartan is effected using the interlattice plane intervals determined by a X-ray powder pattern. Measurement of the X-ray powder patterns was made with a Guinier camera (FR 552 from Enraf Nonius, Delft, NL) on a X-ray film in transmission geometry, using Cu-Ka$_1$ radiation at room temperature. Evaluation of the films for calculation of the interlattice plane intervals is made both visually and by a Line-Scanner (Johansson Täby, S), and the reflection intensities are determined simultaneously. The preferred characterisation of the tetrahydrate of the calcium salt of valsartan $A_{1,Ca}$ is obtained from the interlattice plane intervals d of the ascertained X-ray diffraction diagrams, whereby, in the following, average values are indicated with the appropriate error limits.

The intensities are given in brackets with the following abbreviations: very strong≡vst; strong≡st; medium≡m; weak≡w; and very weak≡vw.

d in [Å]: 16.2±0.3 (vst), 11.4±0.2 (vw), 9.9±0.2 (w), 9.4±0.2 (vw), 8.06±0.1 (vw), 7.73±0.1 (vw), 7.05±0.1 (vw), 6.50±0.05 (vw), 6.36±0.05 (vw), 5.82±0.05 (w), 4.94±0.05 (vw), 4.73±0.05 (vw), 4.33±0.05 (m), 4.17±0.05 (vw), 4.13±0.05 (vw), 3.93±0.05 (vw).

The characteristic reflections in the X-ray diffraction diagram show the following interlattice plane intervals:

d in [Å]: 16.2±0.3, 11.4±0.2, 9.9±0.2, 9.4±0.2, 8.06±0.1, 7.05±0.1, 6.50±0.05, 5.82±0.05, 4.94±0.05, 4.73±0.05, 4.33±0.05, 4.17±0.05, 4.13±0.05, 3.93±0.05.

Another polymorphic form of the tetrahydrate of the calcium salt of valsartan is the solid state form $A_{2,Ca}$. The melting point of form $A_{2,Ca}$ is 195±1.5° C. and the melting enthalpy is 98±8 kJ·Mol$^{-1}$. The indicated melting point is a hydrate melting point which can only be measured in a closed specimen container. Gold containers are used and sample weights of between 2 and 4 mg salt hydrate. The heating rate applied is $T_r$=10 K·min$^{-1}$. For details see the explanations given for the form $A_{1,Ca}$. The tetrahydrate of the calcium valsartan salt $A_{2,Ca}$ reveals the following loss of water as a function of temperature using the thermogravimetric instrument TGS-2 (Perkin-Elmer Corp., Norwalk, Conn. USA) with a heating rate of 10 K·min$^{-1}$, in a water-free $N_2$ atmosphere, the weight loss is illustrated in Table 2.

TABLE 2

| temperature [° C.] | weight loss or water loss in % |
|---|---|
| 25 | 0 ± 0.3 |
| 50 | 0.1 ± 0.3 |
| 75 | 0.5 ± 0.5 |
| 100 | 4.9 ± 0.5 |
| 125 | 11.2 ± 0.5 |
| 150 | 12.2 ± 0.5 |
| 175 | 12.6 ± 0.5 |
| 200 | 12.7 ± 0.5 |
| 225 | 12.8 ± 0.5 |
| 250 | 12.8 ± 0.5 |
| 275 | 13.0 ± 0.5 |

The theoretical water content is for a tetrahydrate of the calcium salt of valsartan 13.2%. The tetrahydrate of the form $A_{2,Ca}$ has a bound water content at 225° C. determined as a weight loss of 12.8% and the total formula is calculated from this $(C_{24}H_{27}N_5O_3)^{2-}Ca^{2+} \cdot (3.9\pm 0.2)H_2O$.

A solid state characterization of the calcium salt of valsartan in form of the tetrahydrate $A_{2,Ca}$ is achieved by a X-ray powder pattern and by the evaluation of the reflections into the interlattice plane intervals. The measurements are throughout made without specific explanations with a Guinier camera (FR 552 from Euraf Nonius, Delft, NL) on an X-ray film in transmission geometry, using Cu-Ka$_1$ radiation at room temperature. Evaluation of the films for calculation of the interlattice plane intervals is made both visually and by a line scanner (Johansson, Täby, S), and the reflection intensities are determined simultaneously. The preferred characterization of the tetrahydrate of the calcium salt of valsartan $A_{2,Ca}$ is obtained from the interlattice plane intervals d of the ascertained X-ray diffraction diagrams, whereby, in the following, values are indicated with the appropriate error limits. The intensities are given in brackets with the following abbreviations: very strong≡vst; strong≡st; medium≡m; weak≡w; and very weak≡vw.

d in [Å]: 16.2±0.3 (vst), 9.9±0.2 (w), 9.4±0.2 (vw), 8.05±0.1 (vw), 7.72±0.1 (vw), 7.04±0.1 (vw) 6.49±0.05 (w), 6.35±0.05 (vw), 5.82±0.05 (w), 4.94±0.05 (vw), 4.73±0.05 (vw), 4.34±0.05 (vw), 4.13±0.05 (m), 3.93±0.05 (w), 3.30±0.05 (vw).

The characteristic reflections in the X-ray diffraction diagram show the following interlattice plane intervals:

d in [Å]: 16.2±0.3, 9.9±0.2, 9.4±0.2, 8.05±0.1, 7.04±0.1, 6.49±0.05, 5.82±0.05, 4.94±0.05, 4.13±0.05, 3.93±0.05.

A new substance has been found as polymorphic form of a trihydrate of the calcium salt of valsartan assigned with $B_{1,Ca}$. The melting point of the substance $B_{1,Ca}$ is measured in a closed sample cell with a heating rate of 10 K·min$^{-1}$ as $T_{fus}$=175±3° C. and the melting enthalpy of the partially crystalline sample is 12±4 kJ·Mol$^{-1}$.

The water content is in theory 10.24% for the trihydrate of the calcium salt of valsartan.

Using the thermogravimetric instrument TGS-2 (Perkin-Elmer Corp., Norwalk, Conn. USA) the water content was determined for the polymorphic form $B_{1,Ca}$ as 9.9±0.4%. A total formula was calculated from this polymorphic form of the trihydrate of the calcium salt of valsartan $(C_{24}H_{27}N_2O_3)^{2-}Ca^{2+}\cdot(2.9\pm0.3)H_2O$.

Using thermogravimetry, in a water-free $N_2$ atmosphere, the weight loss, i.e. the water loss for the trihydrate of the calcium salt of valsartan in the polymorphic form $B_{1,Ca}$ as a function of temperature, was measured at a heating rate of 10 K·min$^{-1}$. The results are illustrated in table 3.

TABLE 3

| temperature [° C.] | weight loss or water loss in % |
|---|---|
| 25 | 0.4 ± 0.3 |
| 50 | 2.0 ± 0.5 |
| 75 | 4.0 ± 0.5 |
| 100 | 6.3 ± 0.5 |
| 125 | 8.5 ± 0.5 |
| 150 | 9.5 ± 0.5 |
| 175 | 9.7 ± 0.5 |
| 200 | 9.9 ± 0.5 |
| 225 | 9.9 ± 0.5 |
| 250 | 10.0 ± 0.5 |
| 275 | 10.3 ± 0.5 |

A solid state characterization of the trihydrate of the calcium salt of valsartan $B_{1,Ca}$ is preferably performed by X-ray powder patterns with the evaluation of the interlattice plane intervals. The measurements have been performed with two samples of the trihydrate $B_{1,Ca}$ of the calcium salt of valsartan and with two different instruments. The first instrument used was a temperature-humidity powder diffraction chamber. X'Pert from Philips Analytical X-ray, 7602 Almelo, NL, equipped with a low and medium temperature attachement from Anton Paar GmbH, A-8054 Graz, Austria. The second instrument is a powder diffractometer PW 1710 also from Philips Analytical X-ray, 7602 Almelo, NL. Two parallel measurements with a reference sample, namely a tetrahydrate of the calcium salt of valsartan have been used to calibrate the powder diffractometer PW 1710 with a Guinier camera (FR 552 from Enraf Nonius, Delft, NL) on a X-ray film in transmission geometry, using Cu-K$\alpha_1$ radiation. The corrections for the interlattice plane intervals to reach the values of the Guinier camera from the powder diffractometer PW1710 were ranging from +0.55 Å for a d-value of 16 Å to +0.02 Å for a d-value of 5.7 Å. No correction was necessary for lower d-values.

The characterization of the trihydrate of the calcium salt of valsartan $B_{1,Ca}$ with the interlattice plane intervals d is as such, whereby, in the following values are indicated with the appropriate error limits. The intensities of the d-values are given in brackets with the following abbreviations: very strong=vst; strong=st; medium=m; weak=w; and very weak=vw.

d in [Å]: 16.0±0.3 (vst), 11.4±0.2 (m), 10.0±0.2 (vw), 9.4±0.2 (vw), 9.1±0.2 (vw), 8.06±0.1 (vw), 7.75±0.1 (vw), 7.03±0.1 (vw), 6.48±0.05 (vw), 6.10±0.05 (vw), 5.76±0.05 (vw), 5.16±0.05 (vw), 4.95±0.05 (vw), 4.75±0.05 (vw), 4.68±0.05 (vw), 4.33±0.05 (vw).

The characteristic reflections in the X-ray diffraction diagram reveal the following interlattice plane intervals for the form $B_{1,Ca}$:

d in [Å]: 16.0±0.3, 11.4±0.2, 10.0±0.2, 9.4±0.2, 8.06±0.1, 7.75±0.1, 7.03±0.1, 6.48±0.05, 6.10±0.05, 5.16±0.05, 4.75±0.05.

The new polymorphic form $B_{2,Ca}$ of a trihydrate of the calcium salt of valsartan has a melting point of 197±1.5° C. measured in a closed sample cell with a Pyris 1 DSC (Differential Scanning calorimeter) from Perkin-Elmer Corp., Norwalk, Conn. USA. The enthalpy of fusion has been determined also from a DSC curve measured also with a heating rate of 10 K·min$^{-1}$ as 62±6 kJ·Mol$^{-1}$. During the DSC measurements of the melting of the trihydrate $B_{2,Ca}$ of the calcium salt of valsartan also a glass transition was observed, as an unequivocal proof of amorphous substance present in this substance. The glass transition temperature was calculated with $T_g$=68±20° C. as the mid point of a change of the specific heat of the substance, namely the trihydrate $B_{2,Ca}$ of the calcium salt of valsartan. The value for the change of the specific heat was calculated as $\Delta c_p$=0.2±0.1 J·(g·K)$^{-1}$. The amorphicity present in the substance $B_{2,Ca}$ approximated by this value for the change of the specific heat is 18±12%. The crystalline trihydrate $B_{2,Ca}$ of the calcium salt of valsartan is according to the heat of fusion measured with the DSC Pyris 1, the main component is this crystalline product, the amorphous part of the calcium salt of valsartan is a minor part.

The water content of the trihydrate $B_{2,Ca}$ of the calcium salt of valsartan is 10.5±0.5%. The value was measured with a thermogravimteric instrument TGS-2 (Perkin-Elmer Corp., Norwalk, Conn. USA). The total formula was calculated from this bound water content for the polymorph of the trihydrate $B_{2,Ca}$ as $(C_{24}H_{27}N_5O_3)^{2-}Ca^{2+}\cdot(3.1\pm0.3)H_2O$.

Water may also be present in the amorphous part of the substance $B_{2,Ca}$, which is depending on the concentration of the non-crystalline part. This water is within the amorphous part differently bound compared to the water molecules in the hydrate form of the crystalline part. As a first approximation one can state, that the crystalline and the amorphous part are similar in the water concentration in case the last process of reaching the state of the material is not passing the anhydrous form of the calcium salt of valsartan. The explanation for this fact is given with the molecular structure of the calcium salt of valsartan, the same holds for the magnesium salt of valsartan, namely that the salt structure is to a considerable part based on the short range order of the molecular interacting substances valsartan, calcium or magnesium and water which is not free water, however structural bound water. This narrow range molecular structure is rather similar for the crystalline part as for the amorphous part. Of course, in the amorphous material, there is a complete lack of long range order in contrary to the crystalline material were any molecule, in the present case, any molecule in trihydrate $B_{2,Ca}$ calcium salt of valsartan is over neighboring molecules structural interrelated with all the molecules within any single crystal.

Using thermogravimetry, in a water-free $N_2$ atmosphere, the weight loss, i.e. the water loss for the trihydrate $B_{2,Ca}$ as a function of temperature, was measured at a heating rate of 10 K·min$^{-1}$. The results for the polymorph $B_{2,Ca}$ of the trihydrate of the calcium salt of valsartan are illustrated in table 4.

TABLE 4

| Temperature [° C.] | Weight loss or water loss in % |
|---|---|
| 25 | 0.1 ± 0.2 |
| 50 | 0.9 ± 0.3 |
| 75 | 2.2 ± 0.5 |
| 100 | 5.8 ± 0.5 |
| 125 | 8.9 ± 0.5 |
| 150 | 9.9 ± 0.5 |
| 175 | 10.2 ± 0.5 |
| 200 | 10.3 ± 0.5 |
| 225 | 10.5 ± 0.5 |
| 250 | 10.5 ± 0.5 |
| 275 | 10.8 ± 0.5 |

TABLE 5

| temperature [° C.] | weight loss or water loss in % |
|---|---|
| 25 | 0.3 ± 0.2 |
| 50 | 1.4 ± 0.3 |
| 75 | 2.8 ± 0.5 |
| 100 | 5.7 ± 0.5 |
| 125 | 8.4 ± 0.5 |
| 150 | 9.4 ± 0.5 |
| 175 | 9.6 ± 0.5 |
| 200 | 9.7 ± 0.5 |
| 225 | 9.8 ± 0.5 |
| 250 | 10.0 ± 0.5 |
| 275 | 10.2 ± 0.5 |

The solid state characterization of the trihydrate of the calcium salt of valsartan $B_{2,Ca}$ was performed by X-ray powder spectroscopy using two different instruments and two different charges produced with the evaluation of the interlattice plane intervals. The first instrument was a powder diffractometer PW 1710 from Philips Analytical X-ray, 7602 Almelo, NL. The second instrument was a Guinier camera FR 552 from Enraf Nonius, Delft, NL on a X-ray film in transmission geometry, using Cu-Ka$_1$ radiation. The first instrument has been calibrated with the Guinier camera, the corrections ranging from +0.55 Å for a d-value of 16 Å to +0.02 Å for a d-value of 5.7 Å. No corrections were necessary for lower d-values. The characterization of the trihydrate of the calcium salt of valsartan $B_{2,Ca}$ with the interlattice plane intervals is as such, whereby, in the following values are indicated with the appropriate error limits. The intensities of the d values are given in brackets with the following abbreviations: very strong=vst; strong=st; medium=m; weak=w; and very weak=vw.

d in [Å]: 16.2±0.3 (vst), 11.5±0.2 (w), 9.9±0.2 (w), 9.4±0.2 (w), 9.0±0.1 (vw), 8.13±0.1 (vw), 7.78±0.1 (vw), 7.04±0.1 (vw), 6.50±0.1 (vw), 6.09±0.05 (vw), 5.79±0.05 (vw), 5.18±0.05 (vw), 4.95±0.05 (vw), 4.74±0.05 (vw), 4.16±0.05 (w).

The characteristic reflections in the X-ray diffraction diagram show the following interlattice plane intervals:

d in [Å]: 16.2±0.3, 11.5±0.2, 9.9±0.2, 9.4±0.2, 7.04±0.1, 6.50±0.1, 5.79±0.05, 4.74±0.05, 4.16±0.05.

Another polymorph of the trihydrate of the calcium salt of valsartan namely the $B_{3,Ca}$ has a melting point measured with a heating rate of 10K·min$^{-1}$ in a hermetically sealed sample cell of 192±1.5° C. The enthalpy of fusion has been determined also by a DSC measurement with 17±4 kJ·Mol$^{-1}$.

The glass transition phenomena observed with the DSC at 65° C. is revealing a change of the specific heat capacity of $sc_p$=0.3 3 g$^{-1}$·K$^{-1}$. Compared with the change of the specific heat capacity of a 100% amorphous calcium salt of valsartan as a trihydrate the amorphous content of the $B_{3,Ca}$ can be estimated with 50%. Therefore the enthalpy of fusion for the crystalline $B_{3,Ca}$ is 34±10 kJ·Mol$^{-1}$.

The water content of the polymorphic form $B_{3,Ca}$ for the trihydrate of the calcium salt of valsartan was determined with a thermobalance from Perkin-Elmer Corp., Norwalk, Conn. USA, named TGS-2 with a value of 9.8±0.5%. The total formula was calculated from this bound water content for the polymorphic from $B_{3,Ca}$ with $(C_{24}H_{27}N_5O_3)^{2-}Ca^{2+}$. $(2.9\pm0.3)H_2O$.

Using thermogravimetry, in a water-free $N_2$ atmosphere, the weight loss, i.e. the water loss for the trihydrate $B_{3,Ca}$ as a function of temperature, was measured at a heating rate of 10 K·min$^{-1}$. The results for the polymorphic form $B_{3,Ca}$ of the trihydrate of the calcium salt of valsartan are illustrated in table 5.

The Guinier camera FR552 with a X-ray film in transmission geometry, using a Cu-Ka$_1$ radiation from Enraf Nonius, Delft, NL has been installed to characterize at room temperature the crystal lattice by the interlattice plane intervals of the calcium salt of valsartan in form of the trihydrate $B_{3,Ca}$.

The reflections in the X-ray diffraction diagram for the trihydrate of the calcium salt of valsartan $B_{3,Ca}$ reveal the following interlattice plane intervals d, whereby, values are indicated with the appropriate error limits. The intensities of the d-values are given in brackets with the following abbreviations: very strong=vst; strong=st; medium=m; weak=w; and very weak=vw.

d in [Å]: 16.1±0.3 (vst), 11.4±0.2 (m), 9.9±0.2 (w), 9.4±0.2 (w), 9.0±0.1 (vw), 8.04±0.1 (vw), 7.73±0.1 (vw), 7.03±0.1 (vw), 6.47±0.05 (vw), 6.33±0.1 (vw), 6.09±0.05 (vw), 5.79±0.05 (w), 5.17±0.05 (vw), 4.95±0.05 (vw), 4.73±0.05 (vw), 4.48±0.05 (vw), 4.33±0.05 (vw), 4.15±0.05 (vw), 4.11±0.05 (vw), 3.94±0.05 (vw), 3.61±0.05 (vw).

The characteristic reflections in the X-ray diffraction diagram show the following interlattice plane intervals:

d in [Å]: 16.1±0.3, 11.4±0.2, 9.9±0.2, 9.4±0.2, 9.0±0.1, 7.03±0.1, 6.47±0.05, 5.79±0.05, 4.15±0.05, 3.94±0.05.

Measurements of the infrared spectrum were performed by means of ATR-IR (Attenuated Total Reflection-Infrared Spectroscopy) using the instrument Spektrum BX from Perkin-Elmer Corp., Beaconsfield, Bucks, England.

The trihydrate of the calcium salt of valsartan $B_{3,Ca}$ has the following ATR-IR adsorption bands expressed in reciprocal wave numbers (cm$^{-1}$):
3594 (w); 3309 (m); 3053 (w); 2959 (w); 2930 (w); 2870 (w); 1621 (m); 1577 (m); 1505 (w); 1458 (m); 1416 (m); 1405 (m); 1354 (w); 1301 (w); 1273 (w); 1210 (w); 1179 (w); 1138 (w); 1104 (w); 1099 (w); 1012 (w); 1003 (w); 974 (w); 941 (w); 906 (w); 856 (w); 841 (w); 756 (m); 737 (m); 667 (m).

The intensities of the absorption bands are indicated as follows: (w)=weak, (m)=medium, and (st)=strong intensity.

The characteristic absorption bands of the ATR-IR spectroscopy for the polymorphic form $B_{3,Ca}$ of the trihydrate of the calcium salt of valsartan are shown by the following values expressed in reciprocal wave numbers (cm$^{-1}$):
3594 (w); 2959 (w); 1621 (st); 1577 (m); 1458 (m); 1405 (m); 1354 (w); 1273 (w); 1012 (w); 756 (m); 737 (m); 667 (m). The error margin for all absorption bands of ATR-IR is ±3 cm$^{-1}$.

Additionally, a new substance has been found as the monohydrate of the calcium salt of valsartan $C_{1,Ca}$.

The bound water content is 3.1±0.3% measured with a thermobalance TGS-2 (Perkin-Emer Corp., Norwalk, Conn., USA). The total formula was calculated from the bound water content for the monohydrate $C_{1,Ca}$ as $(C_{24}H_{27}N_5O_3)^{2-}Ca^{2+}$. $(0.8\pm0.2)H_2O$.

The solid state characterization of the monohydrate of the calcium salt of valsartan $C_{1,Ca}$ was executed by X-ray powder patterns with the evaluation of the interlattice plane intervals.

The instrument used was a temperature-humidity powder diffraction chamber X'Pert from Philips Analytical X-ray, 7602 Almelo, NL, equipped with a low and medium temperature attachement from Anton Paar GmbH, A-8054 Graz, Austria.

The characterization of the monohydrate of the calcium salt of valsartan $C_{1,Ca}$ with the interlattice plane intervals d is as such, whereby, in the following values are indicated with the appropriated error limits. The intensities of the d-values are given in brackets with the following abbreviations: very strong=vst; strong=st; medium=m; weak=w; and very weak=vw.

d in [Å]: 16.0±0.3 (m), 15.0±0.3 (vst), 11.6±0.2 (w), 9.9±0.2 (vw), 9.4±0.2 (vw), 8.02±0.1 (vw), 7.53±0.1 (vw), 7.02±0.1 (vw), 6.47±0.05 (vw), 6.11±0.0.5 (vw), 4.50±0.05 (vw), 4.34±0.05 (vw).

The characteristic reflections in the X-ray diffraction diagram show the following interlattice plane intervals:

d in [Å]: 16.0±0.3, 15.0±0.3, 11.6±0.2, 9.4±0.2, 7.53±0.1, 6.11±0.05.

Surprisingly, another new substance has been found, assigned with $D_{1,Ca}$ being the di-(calcium salt of valsartan) pentahydrate. The melting point of this new substance $D_{1,Ca}$ is $T_{fus}$=210±2° C. measured in a closed sample cell with a heating rate of 10K·min$^{-1}$ and with a DSC called Pyris 1 from Perkin-Elmer Corp., Norwalk, Conn., USA. With the same instrument and the same procedures as above explained, the heat of fusion was determined. The heat of fusion is for the di-(calcium salt of valsartan) pentahydrate for a 100% crystalline di-(calcium salt of valsartan) pentahydrate is approximated with 94 kJ·Mol$^{-1}$.

The water content of the di-(calcium salt of valsartan) as pentahydrate was measured with a thermobalance TGS-2 (Perkin-Elmer Corp., Norwalk, Conn. USA) and gave the value at the plateau of 225° C. of 8.1±0.5%. The total formula was elucidated from this bound water content for the substance $D_{1,Ca}$ as $[(C_{24}H_{27}N_5O_3)^{2-}Ca^{2+}]_2 \cdot (4.7±0.3)H_2O$.

Using thermogravimetry, in a water-free $N_2$ atmosphere, the weight loss, i.e. the water loss for the di-(calcium salt of valsartan) pentahydrate $D_{1,Ca}$ as a function of temperature, was measured at a heating rate of 10 K·min$^{-1}$. The results for the di-(calcium salt of valsartan) pentahydrate are illustrated in table 6.

TABLE 6

| Temperature [° C.] | Weight loss or water loss in % |
|---|---|
| 25 | 0.1 ± 0.1 |
| 50 | 1.3 ± 0.3 |
| 75 | 2.8 ± 0.5 |
| 100 | 5.1 ± 0.5 |
| 125 | 7.4 ± 0.5 |
| 150 | 8.0 ± 0.5 |
| 175 | 8.1 ± 0.5 |
| 200 | 8.2 ± 0.5 |
| 225 | 8.2 ± 0.5 |
| 250 | 8.3 ± 0.5 |
| 275 | 8.6 ± 0.5 |

The solid state characterization of the di-(calcium salt of valsartan) pentahydrate $D_{1,Ca}$ was achieved with a Guinier camera (FR 522 from Enraf Nonius, Delft, NL) on an X-ray film in transmission geometry, using Cu-K$\alpha_1$ radiation at room temperature. Evaluations of the films for calculation of the interlattice plane intervals are made by a line-scanner (Johansson, Täby, S), and the reflection intensities are determined simultaneously. The reflections in the X-ray diffraction diagram could be evaluated to the following interlattice plane intervals d, whereby values are indicated with appropriate error limits. The intensities of the d-values are given in brackets with the following abbreviations: very strong=vst; strong=st; medium=m; weak=w; and very weak=vw.

d in [Å]: 15.5±0.3 (vst), 11.5±0.2 (st), 9.4±0.2 (vw), 9.04±0.1 (w), 7.75±0.1 (vw), 6.46±0.05 (vw), 6.09±0.05 (w), 5.82±0.05 (vw), 5.66±0.05 (vw), 5.16±0.05 (vw), 4.76±0.05 (vw), 4.48±0.05 (vw), 3.83±0.05 (vw), 3.60±0.05 (vw), 3.36±0.05 (vw).

The characteristic reflections in the X-ray diffraction diagram show the following interlattice plane intervals:

d in [Å]: 15.5±0.3, 11.5±0.2, 9.4±0.2, 9.04±0.1, 6.46±0.05, 6.09±0.05, 5.82±0.05, 5.16±0.05, 4.48±0.05, 3.60±0.05.

Another new-type of crystalline, partially amorphous solids are falling into the groups of the magnesium salt hydrate and anhydrate of valsartan. In particular, the hexahydrate of the magnesium salt of valsartan in form of the polymorphic substance $A_{1,Mg}$ is a preferred substance.

The specific optical rotation of hexahydrates of the magnesium salt of valsartan in water measured with a 1% solution at 20° C. is independent of the polymorphic form present as long as it is a hexahydrate $[\alpha]^D_{20}$=−38°.

The thermal behaviour of this salt hydrate in the region of the melting point only reveals a certain chemical and physical instability. The thermal data are thus dependent on the measurement conditions. The instrument used for the calorimetric data is throughout a DSC Pyris 1 (Differential Scanning calorimeter) obtained from Perkin-Elmer Corp., Norwalk, Conn. USA. The measurements are performed with samples enclosed in a sealed gold specimen container with an internal free volume of ca. 22 microliters, with a sample weight of 2 to 4 mg and with a heating rate of $T_r$=10K·min$^{-1}$. The melting point of hexahydrate of the magnesium salt of valsartan in the polymorphic form $A_{1,Mg}$ is 130±3° C. and the enthalpy of fusion is 45±5 kJ·Mol$^{-1}$. The hexahydrate of the magnesium salt of valsartan as the polymorphic form $A_{1,Mg}$ reveals the following loss of water as a function of temperature in using the method of thermogravimetry. The instrument used was a TGS-2 (Perkin-Elmer Corp., Norwalk, Conn. USA) and the measurement was performed in a water free atmosphere. The heating rate selected was 10 K·min$^{-1}$. The weight loss is illustrated in table 7.

TABLE 7

| Temperature [° C.] | Weight loss or water loss in % |
|---|---|
| 25 | 0.1 ± 0.1 |
| 50 | 1.0 ± 0.3 |
| 75 | 6.8 ± 0.5 |
| 100 | 14.1 ± 0.5 |
| 125 | 15.6 ± 0.5 |
| 150 | 16.4 ± 0.5 |
| 175 | 16.9 ± 0.5 |
| 200 | 17.1 ± 0.5 |
| 225 | 17.3 ± 0.5 |
| 250 | 17.6 ± 0.5 |
| 275 | 18.3 ± 0.5 |

The theoretical water content is for the hexahydrate of the magnesium salt of valsartan 19.1%. The hexahydrate of the magnesium salt of valsartan in form of the polymorph $A_{1,Mg}$ has a bound water content at 225° C. determined as a weight loss of 17.3±0.5%.

The total formula is calculated from this as $(C_{24}H_{27}N_5O_3)^{2-}Mg^{2+} \cdot (5.4±0.2)H_2O$.

The solid-state characterization of the magnesium salt of valsartan for the polymorphic form of the hexahydrate $A_{1,Mg}$ is achieved by a X-ray powder pattern and by the evaluation of the reflections into the interlattice plane intervals. The measurements have been made with three different X-ray instruments. The first instrument used is a Guinier camera (FR 522 from Enraf Nonius, Delft, NL) on an X-ray film in transmission geometry, with a Cu-K$\alpha_1$ radiation at room temperature. Evaluations of the films for calculation of the interlattice plane intervals are performed with a scanner from Johansson, Täby, S and the reflections intensities are determined simultaneously. The second instrument used for X-ray measurements of the new substance $A_{1,Mg}$ is a temperature-humidity powder diffraction chamber X'Pert from Philips Analytical X-ray, 7602 Almelo, NL equipped with a low and medium temperature attachement from Anton Paar GmbH, A-8054 Graz. The third instrument applied in the solid state characterization is the powder diffractometer PW1710 from Philips Analytical X-ray. 7602 Almelo, NL. The characterization of the polymorph $A_{1,Mg}$ of the hexahydrate of the magnesium salt of valsartan is achieved from the interlattice plane intervals d of the ascertained X-ray measurements. In the following d values are listed with the appropriate error limits. The intensities are given in brackets with the following abbreviations: very strong=vst; strong=st; medium=m; weak=w; and very weak=vw.

d in [Å]: 19.6±0.3 (vst), 16.6±0.3 (vw), 10.3±0.2 (vw), 9.8±0.2 (m), 7.3±0.1 (w), 6.9±0.1 (vw), 6.01±0.05 (w), 5.92±0.05 (w), 5.55±0.05 (vw), 5.38±0.05 (vw), 5.23±0.05 (vw), 5.15±0.05 (vw), 5.05±0.05 (vw), 4.90±0.05 (m), 4.54±0.05 (vw), 4.22±0.05 (vw), 4.13±0.05 (vw), 4.07±0.05 (w), 3.96±0.05 (vw), 3.73±0.05 (vw), 3.64±0.05 (vw), 3.43±0.05 (w), 3.29±0.05 (vw), 3.22±0.05 (vw), 3.11±0.05 (vw).

The characteristic reflections in the X-ray diffraction diagram reveal the following plane intervals:

d in [Å]: 19.6±0.3, 16.6±0.3, 10.3±0.2, 9.8±0.2, 7.3±0.1, 6.01±0.05, 5.92±0.05, 5.55±0.05, 5.38±0.05, 4.90±0.05, 4.13±0.05, 4.07±0.05, 3.43±0.05.

The substance in form of the tetrahydrate $B_{1,Mg}$ is a partially amorphous solid of the magnesium salt of valsartan. The tetrahydrate $B_{1,Mg}$ shows the following loss of water as a function of temperature measured with a thermobalance TGS-2 (Perkin-Elmer Corp., Norwalk, Conn. USA). The heating rate selected was 10K·min$^{-1}$. The weight loss is tabulated in table 8.

TABLE 8

| Temperature [° C.] | Weight loss or water loss in % |
|---|---|
| 25 | 0 ± 0.1 |
| 50 | 2.1 ± 0.3 |
| 75 | 6.5 ± 0.5 |
| 100 | 9.5 ± 0.5 |
| 125 | 11.1 ± 0.5 |
| 150 | 12.0 ± 0.5 |
| 175 | 12.5 ± 0.5 |
| 200 | 12.8 ± 0.5 |
| 225 | 13.0 ± 0.5 |
| 250 | 13.6 ± 0.5 |
| 275 | 14.3 ± 0.5 |

The magnesium salt of valsartan in the polymorphic form of the tetrahydrate $B_{1,Mg}$ is showing a bound water content at 225° C. of 13.0±0.5%, and as shown for 25° C. in Table 8 practically no additional free water is present in the substance $B_{1,Mg}$. The measurements were performed with a thermobalance TGS-2 of the Perkin-Elmer Corp., CT USA. The total formula is therefore calculated as $(C_{24}H_{27}N_5O_3)^{2-}Mg^{2+}\cdot(3.8\pm0.2)H_2O$.

The solid-state characterization of the tetrahydrate of the magnesium salt of valsartan $B_{1,Mg}$ has been performed with an X-ray instrument by a so-called temperature-humidity powder diffraction chamber X'Pert from Philips Analytical X-ray, 7602 Almelo, NL, equipped with a low and medium temperature attachement from Anton Paar GmbH, A-8054 Graz. Additional X-ray measurements were performed with a powder diffractometer PW 1710 from Philips Analytical X-ray, 7602 Almelo, NL. The crystalline parts of the substance $B_{1,Mg}$ are characterized in the solid state with the interlattice plane intervals d, which are given with appropriate error limits. The intensities are reported in brackets with the following abbreviations: very strong=vst; strong=st; medium=m; weak=w; and very weak=vw.

d in [Å]: 15.8±0.3 (vst), 11.0±0.2 (w), 8.0±0.2 (vw).

The new substance $C_{1,Mg}$ is a the trihydrate of the magnesium salt of valsartan. The water content was measured with a thermobalance TGS-2 (Perkin-Elmer Corp., Norwalk, Conn. USA). The water content for this substance, namely the trihydrate of the magnesium salt of valsartan $C_{1,Mg}$ is 10.7±0.5%. The total formula is calculated from this $(C_{24}H_{27}N_5O_3)^{2-}Mg^{2+}\cdot(3.0\pm0.3)H_2O$.

The solid-state characterization of the trihydrate of the magnesium salt of valsartan $C_{1,Mg}$ has been performed with X-ray measurements by use of the temperature-humidity powder diffraction chamber X'Pert from Philips Analytical X-ray, 7602 Almelo, NL equipped with a low and medium temperature attachement from Anton Paar GmbH, A-8054 Graz.

The characterization of the substance $C_{1,Mg}$ of the magnesium salt of the valsartan trihydrate is given with the interlattice plane intervals d obtained with X-ray measurements. In the following, d values are listed with the appropriate error limits. The intensities are given in brackets with the following abbreviations: very strong=vst; strong=st; medium=m; weak=w; and very weak=vw.

d in [Å]: 17.9±0.3 (m), 10.2±0.2 (w), 8.96±0.2 (m), 7.18±0.1 (w), 6.97±0.1 (vw), 6.81±0.1 (vw), 6.24±0.05 (vw), 5.93±0.05 (w), 5.84±0.05 (w), 5.72±0.05 (vw), 5.59±0.05 (vw), 5.42±0.05 (m), 5.25±0.05 (vw), 5.11±0.05 (m), 5.01±0.05 (st), 4.82±0.05 (w), 4.67±0.05 (w), 4.57±0.05 (vw), 4.49±0.05 (vw), 4.30±0.05 (m), 4.19±0.05 (vst), 4.13±0.05 (vst), 4.02±0.05 (vst), 3.88±0.05 (vw). The characteristic reflections in the X-ray diffraction diagram reveal the following plane intervals:

d in [Å]: 17.9±0.3, 10.2±0.2, 8.96±0.2, 7.18±0.1, 5.93±0.05, 5.84±0.05, 5.42±0.05, 5.11±0.05, 5.01±0.05, 4.82±0.05, 4.67±0.05, 4.30±0.05, 4.19±0.05, 4.13±0.05, 4.02±0.05.

The magnesium salt of valsartan is also forming a substance as a monohydrate which is indicated with $D_{1,Mg}$. The water content was measured with a thermobalance TGS-2 (Perkin-Elmer Corp., Norwalk, Conn. USA). The water content for the monohydrate $D_{1,Mg}$ is 2.8±0.3%. The total formula was calculated from this value with $(C_{24}H_{27}N_5O_3)^{2-}Mg^{2+}\cdot(0.74\pm0.2)H_2O$.

The solid-state characterization of the monohydrate of the magnesium salt of valsartan $D_{1,Mg}$ was achieved with X-ray measurements by use of the temperature-humidity powder diffraction chamber X'Pert from Philips Analytical X-ray, 7602 Almelo, NL. This X-ray instrument is equipped with a low and medium temperature attachement from Anton Paar GmbH, A-8054 Graz.

The characterization of the new substance, namely the monohydrate of the magnesium salt of valsartan $D_{1,Mg}$ is demonstrated with the interlattice plane intervals d of the X-ray investigations. In the following d values are listed with the appropriate error limits. The intensities are given in brackets with the following abbreviations: very strong=vst; strong=st; medium=m; weak=w; and very weak=vw.

d in [Å]: 15.1±0.2 (st), 10.9±0.2 (w), 10.3±0.2 (vw), 7.66±0.1 (vw), 7.21±0.1 (vw), 5.12±0.05 (vw), 4.75±0.05 (vw).

The characteristic reflections in the X-ray diffraction diagram for the monohydrate of the magnesium salt of valsartan reveal the following plane intervals:

d in [Å]: 15.1±0.2, 10.9±0.2, 10.3±0.2, 7.66±0.1, 5.12±0.05.

Surprisingly, the crystalline salts of valsartan can be transformed into amorphous or partially amorphous substances. Crystalline and amorphous forms of corresponding chemical entities reveal different physico-chemical properties, related to the different structures of the crystalline and the amorphous form on a molecular level. The main difference is in the three-dimensional organization of the solid particles. The crystalline particles or crystals reveal a short distance arrangement of a given number of molecules in well defined crystal lattice positions around each single molecule. All these first neighboring molecules of the set of molecules within an elementary cell of a crystal are within the whole crystal lattice in the same geometrical arrangement. The short distance arrangement of any single molecule is in crystal combined with the low range arrangement. In contrary, an amorphous substances reveals only a short range order for each molecule, however, the long range order is not existing within the amorphous solid particles. A consequence of this structural facts is the completely different behaviour of crystals or of an amorphous substance in heating up, starting at a low temperature within the solid phases. Any crystalline substance is characterized with a melting point, which might be different for different polymorphs of the same chemical entity, however, together with the enthalpy of fusion the interrelation to the crystalline phase present is proofed. In contrary, an amorphous substance is never revealing a melting point and a enthalpy of fusion. But, in heating up, starting at a low temperature, an amorphous substance corresponds with a glass transition temperature, a temperature for which the molar heat capacity changes over a certain temperature interval. The broadness of this effect is depending on quite different qualities. The enthalpy change in heating up is for a glass transition always a uptake of energy by the sample. The crystalline and amorphous substances are discriminated at room temperature by several spectroscopical methods such as X-ray, Raman, IR. Additionally, a characterization at elevated temperature over the stability region of crystalline substances in the solid phase is also possible with a temperature-humidity powder diffraction chamber. A preferred characterization are the X-ray methods, because the amorphous substances reveal only a broad reflection, however, the crystalline substances are characterized with a discrete set of interlattice plane intervals.

The solid state characterization of the amorphous entity of the calcium salt hydrate of valsartan $E_{1,Ca}$ is performed with a DSC (Differential Scanning calorimeter) Pyris 1 from Perkin-Elmer Corp., Norwalk, Conn. USA. The same procedure must be executed as for the crystalline salts of calcium valsartan, namely because of existing salt hydrates, with a bound water content up to 13.2%, the measurements must be made in gold containers with a small internal free volume. In the present case, the gold containers had an internal free volume of ca. 22 microliters. Additional water, so-called free water could be present in the amorphous substance, detectable by a thermobalance as well as by the enthalpy of fusion for bulk water at 0° C. In an open sample pan or with a sample pan with a large internal free volume compared with the sample mass and depending on the water of the substance under investigation, the water evaporates partially or completely in transferring the chemical entity present partially or completely into the corresponding anhydrate or into a hydrate with a lower water content. Gold containers with a wall thickness 0.2 mm were used; after weighing the samples between 1.5 and 6 mg salt hydrate, they were sealed by cold welding.

The amorphous substance of the calcium salt of valsartan $E_{1,Ca}$ related to the tetrahydrates and the trihydrates has a water content of 11±2%. The water content is given through the laboratory production process. The glass transition was measured with sample weights of 3-5 mg in sealed gold containers with a internal free volume of ca. 22 microliters and applying a heating rate of 10 K·min$^{-1}$. The glass transition temperature is determined for the amorphous calcium salt of valsartan $E_{1,Ca}$ as $T_g=94\pm20°$ C. and the change of the specific heat capacity is at the glass transition temperature as $\Delta c_p=0.6\pm0.3$ J·g$^{-1}$·K$^{-1}$. No melting point and no enthalpy of fusion could be observed.

The amorphous substance of the calcium salt of valsartan $F_{1,Ca}$ related to the anhydrate has a water content of 9±2%. The water content is measured using thermogravimetry, in a water-free $N_2$ atmosphere with a TGS-2 (Perkin-Elmer Corp., Norwalk, Conn. USA). The glass transition was measured with sample weights of 2-4 mg in sealed gold containers with a internal free volume of ca. 22 microliters and applying a heating rate of 10 K·min$^{-1}$. The glass transition temperature is determined for the amorphous salt of valsartan $F_{1,Ca}$ as $T_g=143\pm20°$ C. and the change of the specific heat capacity is at the glass transition temperature $\Delta c_p=0.4\pm0.15$ J·g$^{-1}$·K$^{-1}$. No melting point and no enthalpy of fusion could be observed. These combined thermodynamic data, melting point and enthalpy of fusion are an absolute prerequisite of a crystalline material or substance.

The amorphous substance of the magnesium salt of valsartan $E_{1,Mg}$ has a water content of 16±3%. The water content is less defined in an amorphous form, as the water molecules in an amorphous substance are weaker bound within the solid structure compared to a crystalline substance forming a hydrate. The water content is measured using thermogravimetry, in a water-free $N_2$ atmosphere with a TGS-2 (Perkin-Elmer Corp., Norwalk, Conn. USA). The glass transition was measured with sample weights of 2-4 mg in sealed gold containers with an internal free volume of ca. 22 microliters and applying a heating rate of 10 K·min$^{-1}$. The glass transition temperature is $T_g=78\pm20°$ C. and the change of the specific heat capacity is at the glass transition temperature $\Delta c_p=0.5\pm0.25$ J·g$^{-1}$·K$^{-1}$. No melting point and no enthalpy of fusion could be observed.

Preferred are polymorphic forms that are essentially free of amorphous forms.

A further object of the invention is the preparation of the salts according to the invention.

The salts or salt hydrates according to the invention, including amorphous or crystalline forms thereof, may be prepared as follows:

To form the salt, the process is carried out in a solvent system, in which the two reactants, namely the acid valsartan and the respective base, are sufficiently soluble. It is expedient to use a solvent or solvent mixture, in which the resulting salt is only slightly soluble or not soluble at all, in order to achieve crystallisation or precipitation. One variant for the salt according to the invention would be to use a solvent in which this salt is very soluble, and to subsequently add an anti-solvent to this solution that is a solvent in which the resulting salt has only poor solubility. A further variant for salt crystallisation consists in concentrating the salt solution, for example by heating, if necessary under reduced pressure, in slowly evaporating the solvent, e.g. at room temperature or at a temperature below room temperature, or by seeding with the addition of seeding crystals, or by setting up water activity required for hydrate formation and/or by seeding with the addition of the corresponding seeding crystals. Combinations of these production steps may be appropriately selected.

The solvents that may be used are for example $C_1$-$C_5$-alkanols, preferably ethanol and isopropanol, as well as $C_1$-$C_5$-dialkylketones, preferably acetone and mixtures thereof with water.

The antisolvents for salt crystallisation may be for example $C_3$-$C_7$-alkylnitriles, especially acetonitrile, esters, especially $C_2$-$C_7$-alkanecarboxylic acid-$C_1$-$C_5$-alkylester, such as ethyl or isopropyl acetate, di-($C_1$-$C_5$-alkyl)-ethers, such as tert.-butylmethylether, furthermore tetrahydrofuran, and $C_5$-$C_8$-alkanes, especially pentane, hexane or heptane.

The dissolving and crystallising process is characterised in that
(i) valsartan and the appropriate base are brought to a reaction in a preferably water-containing, organic solvent,
(ii) the solvent system is concentrated, for example by heating, if necessary under reduced pressure and by seeding with seeding crystals or by slowly evaporating, e.g. at room temperature or at elevated temperatures, then crystallisation or precipitation is initiated and
(iii) the salt or salt hydrate obtained is isolated.

In the dissolving and crystallising process, the water-containing, organic solvent system employed is advantageously a mixtures of alcohols, such as ethanol, and water, or alkylnitrile, especially acetonitrile, and water.

The equilibrating crystallisation process for producing hydrates is characterised in that
(i) valsartan and the appropriate base are added to a water-containing organic solvent,
(ii) the solvent is concentrated, for example by heating, if necessary under reduced pressure or by slowly evaporating, e.g. at room temperature
(iii) the residue of evaporation is equilibrated with the required amount of water by
(a) suspending the residue of evaporation, which is advantageously still warm, and which still contains some water, in an appropriate solvent or
(b) by equilibrating the water excess in the solvent at a given temperature, or with cooling from a given elevated temperature to a lower one;
whereby in a) and b) the existing or added water is present in a quantity in which the water dissolves in the organic solvent and does not form an additional phase; and
(iv) the salt obtained is isolated.

The solvent system used as the water-containing organic solvent advantageously comprises mixtures of suitable alcohols, such as $C_1$-$C_7$-alkanols, especially ethanol, and water.

An appropriate solvent for equilibration is, for example, an ester such as $C_1$-$C_7$-alkanecarboxylic acid-$C_1$-$C_7$-alkylester, especially ethyl acetate, or a ketone such as di-$C_1$-$C_5$-alkylketone, especially acetone.

The equilibration process is notable for example for its high yields and outstanding reproducibility.

Especially, the alkaline earth metal salts of the present invention may be obtained in crystalline form as explained above and are in the form of hydrates, or mixtures of hydrates, or mixtures of hydrates with amorphous forms, from appropriate solvents that are conventionally used in production processes, such as esters, e.g. $C_1$-$C_7$-alkanecarboxylic acid-$C_1$-$C_7$-alkylesters, especially ethyl acetate, ketones, e.g. di-$C_1$-$C_5$-alkylketones, especially acetone, $C_3$-$C_7$-alkylnitriles, especially acetonitrile, or ethers, e.g. di-($C_1$-$C_5$-alkyl)-ethers, such as tert.-butylmethylether, also tetrahydro-furan, or mixtures of solvents. By using the dissolving and crystallising process, or the water-equilibrating crystallisation process, the defined hydrates, which are present in crystalline and in polymorphous forms, may be obtained reproducibly.

The processes for forming salts are likewise objects of the present invention.

These salts or salt hydrates according to the invention are obtained for example by neutralising the acid valsartan with a base corresponding to the respective cation. This neutralisation is suitably effected in an aqueous medium, e.g. in water or a mixture of water and a solvent in which valsartan is more soluble than in water. Salts with weaker bases may be converted into other salts either by treating with stronger bases or by treating with acids and then neutralising with other bases.

Crystallisation, especially of the alkaline earth salt hydrates, is effected in water or an aqueous medium, which consists of water and at least one solvent that is miscible or partially miscible with water, i.e. not too non-polar, e.g. an alkanol such as methanol, ethanol, propanol, isopropanol, butanol, acetone, methyl ethyl ketone, acetonitrile, DMF, DMSO. The alkanol portion amounts to about 10% to 99%, or 20% to 90%, advantageously 30% to 70% by volume. For higher alkanols, the less polar solvent may also be present in lower concentrations. Owing to the restricted water-solubility of valsartan, the process frequently takes place in suspensions, or if valsartan is soluble in the other solvent component, in a solution.

In one embodiment, for example to produce the calcium salt of valsartan, an aqueous solution of valsartan is neutralised with a calcium hydroxide solution at room temperature and the solution is left to crystallise. In a preferred procedure, crystallisation is effected from a solvent mixture of water/ethanol, the ethanol proportion amounting to ca. 30% to 50% by volume. In an especially preferred form, crystallisation is effected in a closed system by transporting through a low temperature gradient (especially 1-2° C. at 40° C.) in 30% by volume of ethanol.

In a preferred variant, crystallisation may be optimised, e.g. accelerated, by adding at least one seed crystal.

To produce a salt of valsartan in a desired form as a hydrate, or an anhydrate and in a specific polymorph, or in a specific amorphous form thereof, a dissolving, chemical reaction, and crystallising process is used in particular, or a water-equilibrating crystallization, or an additional drying-equilibrating process. In the following, the processes consecutive to the dissolving and the chemical reaction shall be outlined:

(i) Transferring the obtained salthydrate, with a given molecular ratio water to salt of valsartan or with a mixture of hydrates, having different molecular ratios of water to salt of valsartan, or as a mixture of hydrates and the anhydrate of the given salt of valsartan, and all these entities and mixtures of entities in a specific polymorphic form, or in a specific amorphous form, or as mixtures of different polymorphs and different amorphous forms with or without a separation from the mother liquid into another liquid phase in which a considerable amount of the solid phase will not be dissolved, however, is present as a suspension. The liquid phase of this suspension is changed stepwise or continuously in appropriate conditions such as temperature, pressure, volume, composition in respect to water, solvents, antisolvents in such a way that the salthydrate of choice is generated by a recrystallization process. The recrystallization can be forced by adding at least one seeding crystal.

(ii) Separate the obtained salthydrate in the crystalline state from the mother liquid, or from the liquid phase in which the salthydrate is suspended and transfer the wet cake with or without washing into a drier. The drier preferably used is a moving product drier, such as an example a paddle drier. The conditions in the drier and for the drying process have to be appropriate selected to obtain the salthydrate in the form to be produced.

In a preferred embodiment of the present invention, the different hydrates and polymorphic and amorphic forms thereof can be prepared by using the thermobalance procedure as follows:

Starting from e.g. the $A_{0,Ca}$ or the $A_{0,Mg}$ form, respectively, said forms are (i) dehydrated, e.g. totally or partially, for example, in a thermobalance apparatus e.g. TGS-2, or in a temperature-humidity powder diffraction chamber, e.g. X'Pert, or in Differential Scanning calorimeter, e.g. DSC Pyris 1;

then (ii) equilibrated by exposure to different relative air humidities over different periods of time, optionally (iii) relaxed over different periods of time, and then, if necessary, (iv) isolated.

The dehydration step is carried out essentially by dehydrating the corresponding starting material in a water free atmosphere, under inert gas, in a defined temperature range and over a defined time intervals. A suitable temperature is from room temperature to 100° C. Suitable time intervals are from 30 minutes to 70 hours.

The equilibration step is carried out by exposing the dehydrated form to different air humidities. Preferred air humidities range from 20% to 70% relative air humidity.

The relaxation period is between 30 minutes to 50 hours. The preferred temperature range for the equilibration step is between 20° C. and 25° C.

The form according to the present invention is preferably isolated by crystallisation.

Important conditions among others are the relative humidity of the atmosphere in the drier, the temperature of the atmosphere and the temperature of the dry product, all these parameters as a function of the drying degree and also the drying time interval which also defines the final state of the equilibrated product.

The main driving force for a hydrate formation of a salthydrate of valsartan during the crystallization or precipitation process, or during a recrystallization process as a suspension or as a product in a drying process is the activity of the water in the liquid phase or the partial pressure of the water in the atmosphere of a drier. The composition of the liquid phase in which the salthydrate of valsartan is suspended and its temperature are decisive for the activity of the water. In the drier, the partial pressure of the water is adjusted under equilibrium or non-equilibrium conditions with conditions such as relative humidity of the inlet gas stream, the temperature of the drier and the temperature of the substance dried, the uptake of water or the dehydration of the substance dried, the flow rate of the atmosphere and the mass of the substance dried. Of course, also the ratio of the water molecules to the salt molecules at the beginning and the end of the drying process and the kinetic of the dehydration or hydration are factors influencing the partial pressure of the water in the drier.

An additional thermodynamic parameter, which is decisive for the salt hydrate of valsartan and the polymorphic form of the final state of the product, is the temperature. The thermodynamic stability regions of the salthydrates of valsartan are depending also on temperature, or in other words certain salthydrates of valsartan and polymorphs thereof are only stable for given temperature regions. As an example, a selected salthydrate of valsartan can only be crystallized or can only be recrystallized also from a solution if the temperature is selected properly.

The salts according to the invention may be used e.g. in the form of pharmaceutical preparations, which contain the active substance e.g. in a therapeutically effective amount of the active substance, optionally together with a pharmaceutically acceptable carrier, for example with an inorganic or organic, solid or optionally also liquid pharmaceutically acceptable carrier, which is suitable for enteral, e.g. oral, or parenteral administration.

The invention relates in particular to a pharmaceutical composition, especially in a solid dosage unit, preferably for oral administration, optionally together with a pharmaceutically acceptable carrier.

Pharmaceutical preparations of this kind may be used for example for the prophylaxis and treatment of diseases or conditions which may be inhibited by blocking the $AT_1$ receptor for example a disease or condition selected from the group consisting of (a) hypertension, congestive heart failure, renal failure, especially chronic renal failure, restenosis after percutaneous transluminal angioplasty, and restenosis after coronary artery bypass surgery;

(b) atherosclerosis, insulin resistance and syndrome X, diabetes mellitus type 2, obesity, nephropathy, renal failure, e.g. chronic renal failure, hypothyroidism, survival post myocardial infarction (Ml), coronary heart diseases, hypertension in the elderly, familial dyslipidemic hypertension, increase of formation of collagen, fibrosis, and remodeling following hypertension (antiproliferative effect of the combination), all these diseases or conditions associated with or without hypertension;

(c) endothelial dysfunction with or without hypertension, (d) hyperlipidemia, hyperlipoproteinemia, atherosclerosis and hypercholesterolemia, and (e) glaucoma.

Primary usages are for the treatment of high blood pressure and congestive heart failure, as well as post-myocardial infarction.

The person skilled in the pertinent art is fully enabled to select a relevant and standard animal test model to prove the hereinbefore and hereinafter indicated therapeutic indications and beneficial effects.

The pharmaceutical activities as effected by administration of representatives of the salts of the present invention or of the combination of active agents used according to the present invention can be demonstrated e.g. by using corresponding pharmacological models known in the pertinent art. The person skilled in the pertinent art is fully enabled to select a relevant animal test model to prove the hereinbefore and hereinafter indicated therapeutic indications and beneficial effects.

These beneficial effects can, for example, be demonstrated in the test model as disclosed by G. Jeremic et al. in J. Cardovasc. Pharmacol. 27:347-354, 1996.

For example, the valuable potential of the salts or combinations of the present invention for the prevention and treatment of myocardial infarction can be found using the following test model.

Study Design

In the study to be performed, permanent coronary artery occlusion (CAO) in rats is used as a model of acute myocardial infarction. The experiments are carried out with 5 treatment groups characterized by following features:
- sham-operated animals
- CAO+vehicle
- CAO+a salt according to the present invention, optionally
- CAO+a salt according to the present invention+a combination partner.

During the study following variables are measured:
- infarct size
- LV chamber volume
- interstitial and perivascular collagen density in spared LV myocardium
- COL-I and COL-III protein content in spared LV myocardium by Western blot
- cardiomyocytes cross-sectional area and length in sections of LV myocardium
- plasma concentrations of renin and aldosterone
- urine concentration of sodium, potassium and aldosterone
- blood pressure in conscious animals
- LV and carotid blood pressure in anesthetized animals.

Methodology

Infarct size: Six μm-thick transverse histological sections of the left ventricle are stained with nitroblue tetrazolium and acquired by a B/W XC-77CE CCD video camera (Sony). The resulting image is processed on a KS 300 image analysis system (Carl Zeiss Vision) using a software specifically developed (Porzio et al., 1995). A single operator blinded to treatment interactively defines the boundaries of the interventricular septum, and the infarcted area on each section is semiautomatically identified as the area of unstained ventricular tissue. The software automatically calculates for each component of the ventricular section defined as the chamber, septum, infarcted area, infarcted LV wall and viable LV wall, a set of geometric parameters (Porzio et al., 1995).

Histology: Hearts are fixed in situ, by retrograde perfusion with buffered 4% formaldehyde after arrest in diastole by i.v. injection of 0.5 M KCl. After fixation, the left ventricle (LV) and the free wall of the right ventricle are separately weighed; LV longer diameter is measured with a caliper. LV histological sections are stained with hematoxylin & eosin for qualitative examination and to quantify cardiomyocytes cross-sectional area with a semi-automated image analysis routine. Interstitial collagen deposition in LV is evaluated on Sirius red stained sections with a semi-automated image analysis routine (Masson et al., 1998).

Collagen content in LV spared myocardium: LV tissue in the spared myocardium is homogenized, subjected to PAGE-SDS electrophoresis and electroblotted onto nitrocellulose membrane. The blots are exposed to primary antibodies, i.e. rabbit anti-rat collagen type I or type III antiserum (Chemicon). The primary antibodies are recognized by secondary antibodies conjugated to alkaline phosphatase (for collagen type I) or peroxidase (collagen type III).

Left ventricular chamber volume: LV chamber volume is determined in hearts arrested in diastole (KCl) and fixed in formalin under a hydrostatic pressure equivalent to the measured LV end-diastolic pressure. A metric rod is inserted into the LV to measure LV inner length. The transverse diameters of the LV chamber are measured in two 1-mm thick transverse sections near to the base and the apex of the ventricle (Jeremic et al., 1996). The chamber volume is computed from an equation integrating transverse diameters and inner length.

Systemic and Left ventricular hemodynamics: A microtip pressure transducer (Millar SPC-320) connected to a recorder (Windograf, Gould Electronics) is inserted into the right carotid artery to record systolic and diastolic blood pressures. The pressure transducer is advanced into the LV to measure LV systolic (LVSP) and end-diastolic (LVEDP) pressures, the first derivative of LV pressure over time (+dP/dt) and heart rate.

Non-invasive blood pressure: Systolic blood pressure and heart rate are measured by the tail-cuff method (Letica LE 5002) in conscious rats.

Urine electrolytes, hormones: Rats are individually housed in metabolic cages and 24-h urine collected on 1 ml HCl 6N. Water intake is measured. Urine catecholamines are extracted on Bondelut $C_{18}$ columns (Varian), separated by HPLC (Apex-II C18, 3 μm, 50×4.5 mm analytical column, Jones Chromatography) and quantified with an electrochemical detector (Coulochem II, ESA) (Goldstein at al., 1981). Plasma and urine aldosterone, and plasma angiotensin II is determined with specific radioimmunoassays (Aldoctk-2, DiaSorin and Angiotensin II, Nichols Diagnostics). Urine sodium and potassium are measured by flame photometry.

Sample Size 10 animals analyzable in each treatment groups are sufficient to detect biologically significant differences. Only rats with an infarct size of at least 10% of the LV section area are included in the final analysis.

Endothelial dysfunction is being acknowledged as a critical factor in vascular diseases. The endothelium plays a bimodal role as the source of various hormones or by-products with opposing effects: vasodilation and vasoconstriction, inhibition or promotion of growth, fibrinolysis or thrombogenesis, production of anti-oxidants or oxidising agents. Genetically predisposed hypertensive animals with endothelial dysfunction constitute a valid model for assessing the efficacy of a cardiovascular therapy.

Endothelial disfunction is characterized by, for example, increased oxidative stress, causing decreased nitric oxide, increased factors involved in coagulation or fibrinolysis such as plasminogen activating inhibitor-1 (PAI-1), tissue factor (TF), tissue plasminogen activator (tPA), increased adhesion molecules such as ICAM and VCAM, increased growth factors such as bFGF, TGFb, PDGF, VEGF, all factors causing cell growth inflammation and fibrosis.

The treatment e.g. of endothelian dysfunction can be demonstrated in the following pharmacological test:

Material and Methods

Male 20-24 week-old SHR, purchased from RCC Ldt (Füllingsdorf, Switzerland), are maintained in a temperature- and light-controlled room with free access to rat chow (Nafag 9331, Gossau, Switzerland) and tap water. The experiment is performed in accordance with the NIH guidelines and approved by the Canton Veterinary office (Bew 161, Kantonales Veterinäramt, Liestal, Switzerland). All rats are treated with the NO synthesis inhibitor L-NAME (Sigma Chemicals) administered in drinking water (50 mg/l) for 12 weeks. The average daily dose of L-NAME calculated from the water consumed was 2.5 mg/kg/d (range 2.1-2.7).

The rats can be divided into 2 or 3 groups: group 1, control (n=e.g. 40); Group 2, a salt according to the present invention; n=e.g. 40); for testing combinations Group 3, combination partner; (n=e.g. 30). The drugs are administered in drinking fluid. The pressure effect of Ang II at 1 mg/kg obtained in controls normotensive rats can be reduced after treatment with a salt according to the present invention (Gervais et al. 1999).

Body weight is measured every week. Systolic blood pressure and heart rate are recorded by tail cuff plethysmography 3 and 2 weeks before starting the study and at 2 weeks after drug administration. Urine is collected over a 24 hour period from rats kept in individual (metabolic) cages the week before starting treatment and at weeks 4 and 12 for volume measurement and protein, creatinine, sodium and potassium determination using standard laboratory methods. At the same time points, blood samples are withdrawn from the retro-orbital plexus (maximum 1 ml) for creatinine, $Na^+$ and $K^+$ assays.

Ten rats from each group are sacrificed at 4 weeks for collection of kidney and heart for morphological analysis. The remaining rats are sacrificed at 12 weeks. Cardiac and kidney weight is recorded. Terminal blood sampling is performed in 5% EDTA at 4 (morphometry study) and 12 (end of the study) weeks for aldosterone, determination by radioimmunoassay using a DPC coat-a-count aldosterone-RIA kit (Bühlmann, Switzerland).

Statistical Analysis:

All data are expressed as mean±SEM. Statistical analysis is performed using a one-way ANOVA, followed by a Duncan's multiple range test and a Newman-Keuls test, 7 for comparison between the different groups. Results with a probability value of less than 0.05 are deemed statistically significant.

An improvement of regression of artherosclerosis without effecting the serum lipid levels can, for example, be demonstrated by using the animal model as disclosed by H. Kano et al. in Biochemical and Biophysical Research Communications 259, 414-419 (1999).

That the salts or combinations according to the present invention can be used for the regression of a cholesterol diet-induced atherosclerosis, can be demonstrated using the test model described, e.g., by C. Jiang et al. in Br. J. Pharmacol. (1991), 104, 1033-1037.

That the salts or combinations according to the present invention can be used for the treatment of renal failure, especially chronic renal failure, can be demonstrated using the test model described, e.g., by D. Cohen et al. in Journal of Cardiovascular Pharmacology, 32: 87-95 (1998).

The present pharmaceutical preparations which, if so desired, may contain further pharmacologically active substances, are prepared in a manner known per se, for example by means of conventional mixing, granulating, coating, dissolving or lyophilising processes, and contain from about 0.1% to 100%, especially from about 1% to about 50%, of lyophilisates up to 100% of the active substance.

The invention similarly relates to compositions containing the salts according to the invention.

The invention similarly relates to the use of the salts according to the invention preferably for the production of pharmaceutical preparations, especially for the prophylaxis and also for the treatment of diseases or conditions which may be inhibited by blocking the $AT_1$ receptor. Primary usages are for the treatment of high blood pressure and congestive heart failure, as well as post-myocardial infarction.

The invention similarly relates to the use for the prophylaxis and treatment of diseases or conditions which may be inhibited by blocking the $AT_1$ receptor, characterised in that a patient, including a human patient, requiring such treatment is administered with a therapeutically effective amount of a salt according to the invention, optionally in combination with at least one composition for the treatment of cardiovascular diseases and related conditions and diseases listed hereinbefore or hereinafter.

The invention similarly relates to combinations, e.g. pharmaceutical combinations, containing a salt of the present invention or in each case a pharmaceutically acceptable salt thereof in combination with at least one composition for the treatment of cardiovascular diseases and related conditions and diseases as listed hereinbefore or hereinafter, or in each case a pharmaceutically acceptable salt thereof. Combinations with other compositions for the treatment of cardiovascular diseases and related conditions and diseases as listed hereinbefore or hereinafter, or in each case a pharmaceutically acceptable salt thereof, are likewise objects of the present invention.

The combination may be made for example with the following compositions, selected from the group consisting of a:
(i) HMG-Co-A reductase inhibitor or a pharmaceutically acceptable salt thereof,
(ii) angiotensin converting enzyme (ACE) Inhibitor or a pharmaceutically acceptable salt thereof,
(iii) calcium channel blocker or a pharmaceutically acceptable salt thereof,
(iv) aldosterone synthase inhibitor or a pharmaceutically acceptable salt thereof,
(v) aldosterone antagonist or a pharmaceutically acceptable salt thereof,
(vi) dual angiotensin converting enzyme/neutral endopeptidase (ACE/NEP) inhibitor or a pharmaceutically acceptable salt thereof,
(vii) endothelin antagonist or a pharmaceutically acceptable salt thereof,
(viii) renin inhibitor or a pharmaceutically acceptable salt thereof, and
(ix) diuretic or a pharmaceutically acceptable salt thereof.

HMG-Co-A reductase inhibitors (also called □-hydroxy-□-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone to by hydroxylating cortocosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

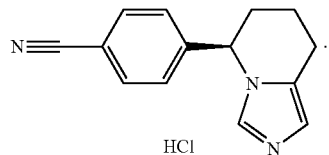

A preferred steroidal aldosterone antagonist is eplerenone of the formula

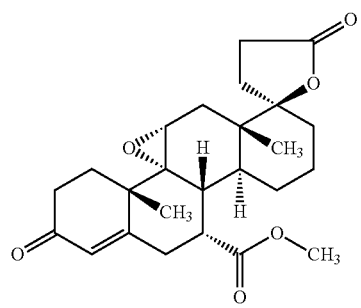

or spironolactone.

A preferred dual angiotensin converting enzyme/neutral endopetidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

A renin inhibitor is, for example, a non-peptidic renin inhibitor such as the compound of formula

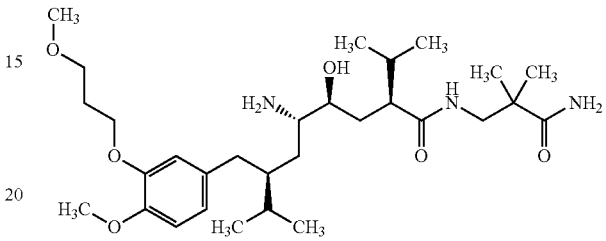

chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide. This representative is specifically disclosed in EP 678503 A. Especially preferred is the hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

Preferably, the jointly therapeutically effective amounts of the active agents according to the combination of the present invention can be administered simultaneously or sequentially in any order, separately or in a fixed combination.

The structure of the active agents identified by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The corresponding active ingredients or a pharmaceutically acceptable salts thereof may also be used in form of a solvate, such as a hydrate or including other solvents, used for crystallization.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

In a variation thereof, the present invention likewise relates to a "kit-of-parts", for example, in the sense that the components to be combined according to the present invention can be dosed independently or by use of different fixed combinations with distinguished amounts of the components, i.e. simultaneously or at different time points. The parts of the kit of parts can then e.g. be administered simultaneously or chronologically staggered, that is at different time points and with equal or different time intervals for any part of the kit of parts.

Preferably, the time intervals are chosen such that the effect on the treated disease or condition in the combined use of the parts is larger than the effect that would be obtained by use of only any one of the components.

The invention furthermore relates to a commercial package comprising the combination according to the present invention together with instructions for simultaneous, separate or sequential use.

Dosaging may depend on various factors, such as mode of application, species, age and/or individual condition. For oral application, the doses to be administered daily are between ca. 0.25 and 10 mg/kg, and for warm-blooded animals with a body weight of ca. 70 kg, preferably between ca. 20 mg and 500 mg, especially 40 mg, 80 mg, 160 mg and 320 mg based on the free acid.

The invention is illustrated in particular by the examples and also relates to the new compounds named in the examples and to their usage and to methods for the preparation thereof.

The following examples serve to illustrate the invention without limiting the invention in any way.

PRODUCTION OF STARTING MATERIAL

Starting materials for all new salthydrates of calcium valsartan and magnesium valsartan have been produced in the following manner. Additionally, the start materials have been characterised by several analytical methods.

Example SM1 (for Starting Material)

Production Example as Start Material for the Calcium Salt as the Tetrahydrate $A_{0,Ca}$ In Situ of (S)—N-(1-carboxy-2-methyl-prop-1-yl)-N-pentanoyl-N-[2'-(1H-tetrazol-5-yl)-biphenyl-4-ylmethyl]amine 21.775 g of (S)—N-(1-carboxy-2-methyl-prop-1-yl)-N-pentanoyl-N-[2'-(1H-tetrazol-5-yl)-biphenyl-4-ylmethyl]-amine are dissolved at room temperature in 300 ml of ethanol. By careful addition of 300 ml of water, the ethanol concentration is reduced to 50% by volume. Using a magnetic stirrer, 3.89 g of $Ca(OH)_2$ are added slowly in small portions to this clear, slightly acidic (pH 4) solution, so that the pH value temporarily does not exceed a value of ca. 8. Because it absorbs $CO_2$ from the air, the $Ca(OH)_2$ used contains traces of $CaCO_3$; therefore the added amount includes an excess of 5%. After adding the stoichiometric amount of $Ca(OH)_2$, the pH is ca. 6, and after adding the excess it rises to 7. The solution becomes turbid through the small amount of finely divided $CaCO_3$, which is removed through a folded filter. The product contained in the solution crystallises continuously upon removal of the alcohol content by allowing to stand at room temperature. The procedure can be accelerated by using a flat dish in a recirculating air drier at 40° C. After concentrating to ca. one half, the alcohol content of the solution drops to ca. 10% by volume and most of the product crystallises. It is filtered, rinsed for a short time with 10% by volume ethanol and dried at 40° C. until reaching a constant weight. (S)—N-(1-carboxy-2-methyl-prop-1-yl)-N-pentanoyl-N-[2'-(1H-tetrazol-5-yl)-biphenyl-4-ylmethyl]-amine calcium salt tetrahydrate $A_{0,Ca}$ is obtained.

The melting point for the tetrahydrate of the calcium salt of valsartan $A_{0,Ca}$, produced according to the above given example for the start material, for a heating rate of 10 K·min$^{-1}$, and in a closed specimen container with a small internal volume of ca. 22 microliters is determined as $T_{fus}$=205° C. and the melting enthalpy as $\Delta_{fus}H$=92 kJ·mol$^{-1}$. The density of the crystals of the tetrahydrate $A_{0,Ca}$ of the calcium salt of (S)—N-(1-carboxy-2-methyl-prop-1-yl)-N-pentanoyl-N-[2'-(1H-tetrazol-5-yl)-biphenyl-4-yl-methyl]-amine, produced according to the example for start materials, determined by a helium pycnometer is 1.297 g·cm$^3$. The specific optical rotation of the tetrahydrate of the calcium salt of valsartan $A_{0,Ca}$ according to this production example is measured at 20° C. in methanol as a 1% solution $[\alpha]^{20}_D$=+1° and in water also at 20° C. as a 0.4% solution $[\alpha]^{20}_D$=−39°.

The enantiomer purity of the salt hydrate produced according to the process for the start materials, namely the tetrahydrate of the calcium salt of valsartan $A_{0,Ca}$ is determined by a stereo-specific HPLC method. The stereo-specific separation is achieved by a chiral column (Chiral AGP). The enantiomer purity for $A_{0,Ca}$ is determined as ee=100%.

The measurement of the infrared spectrum took place by means of ATR-IR (Attenuated Total Reflection-Infrared Spectroscopy) using the instrument BX from Perkin-Elmer Corp., Beaconsfield, Bucks, England.

The characteristic absorption bands of the ATR-IR spectroscopy are listed below for the tetrahydrate of the calcium salt of valsartan $A_{0,Ca}$ produced according to the example SM1 with the following values expressed in reciprocal wave numbers (cm$^{-1}$):

3594; 3306; 2954; 1621; 1578; 1458; 1441; 1417; 1364; 1319; 1274; 1211; 1180; 1137; 1012; 1002; 758; 738; 696; 666.

The water content is in theory 13.2% for the tetrahydrate of the calcium salt of valsartan. Using the thermobalance TGS-2 (Perkin-Elmer Corp., Norwalk, Conn. USA) the water content was determined as 13.0%. A total formula was calculated for the tetrahydrate of the calcium salt of valsartan $A_{0,Ca}$ from this as $(C_{24}H_{27}N_5O_3)^{2-}Ca^{2+}.3.9H_2O$.

Using thermogravimetry, in a water-free $N_2$ atmosphere, the weight loss, i.e. the water loss for the tetrahydrate as a function of temperature, was measured at a heating rate of 10 K·min$^{-1}$. The results for the calcium salt of valsartan tetrahydrate $A_{0,Ca}$ are listed in the following:

| Temperature [° C.] | weight loss or water loss in % |
| --- | --- |
| 25 | 0 |
| 50 | 0 |
| 75 | 0.5 |
| 100 | 3.5 |
| 125 | 10.2 |
| 150 | 12.4 |
| 175 | 12.8 |
| 200 | 12.9 |
| 225 | 13.0 |
| 250 | 13.3 |
| 275 | 13.2 |

Calculation of the interlattice plane intervals from the X-ray powder pattern taken with a Guinier camera is as follows for the characteristic lines for the batch of the substance $A_{0,Ca}$ as tetrahydrate of the calcium salt of valsartan:

d in [Å]: 16.27, 9.90, 9.39, 8.04, 7.71, 7.05, 6.49, 6.34, 6.20, 5.87, 5.75, 5.66, 5.20, 5.05, 4.95, 4.73, 4.55, 4.33, 4.15, 4.12, 3.95, 3.91, 3.87, 3.35.

Elementary analysis gives the following measured values of the elements present in calcium-valsartan-tetrahydrate and of water. The water evaluation was carried out at 130° C. after expulsion. The findings of the elementary analysis, within the error limits, correspond to the sum formula $(C_{24}H_{27}N_5O_3)^{2-}Ca^{2+}.4H_2O$.

| | % found | % calculated |
|---|---|---|
| C | 52.82 | 52.83 |
| H | 6.42 | 6.47 |
| N | 12.91 | 12.83 |
| O | 20.20 | 20.53 |
| water | 13.25 | 13.21 |
| Ca | 7.03 | 7.35 |

Example SM2 (for Starting Material)

Production Example of the Magnesium Salt as the Hexahydrate $A_{0,Mg}$ in situ of (S)—N-(1-carboxy-2-methyl-prop-1-yl)-N-pentanoyl-N-[2'-(1H-tetrazol-5-yl)-biphenyl-4-ylmethyl]-amine 43.55 g of valsartan (S)—N-(1-carboxy-2-methyl-prop-1-yl)-N-pentanoyl-N-[2'-(1H-tetrazol-5-yl)-biphenyl-4-ylmethyl]-amine are dissolved at room temperature in 600 ml of 50% by volume ethanol (from absolute ethanol—see Merck and quarz-bidistilled water). The slightly turbid solution becomes clear after adding a further 50 ml of 50% ethanol. Using a magnetic stirrer, 4.03 g or 0.1 M MgO (Merck p.a.) are slowly added in small portions to this slightly acidic solution with a pH value of 4. The pH value hereby rises to ca. 6. The process is effected with an excess of 10%, i.e. a further 0.40 g of MgO are added. This excess is not fully dissolved, and the pH value rises to ca. 7.5. The small residue is filtered from the solution through a folded filter and washed with 50 ml of 50% ethanol.

The combined clear solution is carefully concentrated at 40° C. whilst stirring with a magnetic stirrer in a large crystallisation dish. Towards the end of this procedure, the solution has a tendency to harden into a glassy gel. Scratching with a glass rod induces the in situ crystallisation in this phase, which may be recognised by the white colour of the crystalline solid thus formed. The product is dried at 50° C. in a recirculating air drier until reaching a constant weight. The yield of magnesiumsalt as the hexahydrate $A_{0,Mg}$ of (S)—N-(1-carboxy-2-methyl-prop-1-yl)-N-pentanoyl-N-[2'-(1H-tetrazol-5-yl)-biphenyl-4-ylmethyl]-mine is 53.7 g or 95% based on the valsartan employed as the free acid.

The melting point of the salt hydrate $A_{0,Mg}$ produced according to the above given procedure, namely the magnesium-valsartan-hexahydrate, for a heating rate of 10 in a sealed sample container with a small internal volume, in an amount of 2.24 mg, was measured at $T_{fus}$=132° C. and a melting enthalpy at $\Delta_{fus}H$=64 kJ·mol$^{-1}$. The density of the crystals of the hexahydrate of the magnesium salt of valsartan produced according to example SM2, determined by a helium pycnometer, is 1.273 g·cm$^3$.

The specific optical rotation of the magnesium-valsartan-hexahydrate $A_{0,Mg}$ produced according to the above example for start materials is measured as a 1% solution in methanol $[\alpha]^{20}_D$=-14° and with the same concentration in water as $[\alpha]^{20}_D$=-38°.

The enantiomer purity of the magnesium salt of valsartan hexahydrate $A_{0,Mg}$ produced according to the process for the start materials is determined by a stereo-specific HPLC method. The stereo-specific separation is achieved by a chiral column (Chiral AGP). The enantiomer purity is determined as ee=99.6%.

The measurement of the infrared spectrum took place by means of ATR-IR (Attenuated Total Reflection-Infrared Spectroscopy) using the instrument Spektrum BX from Perkin Elmer Corp., Beaconsfield, Bucks, England.

The starting material, the hexahydrate of the magnesium salt of valsartan $A_{0,Mg}$ has the following characteristic absorption bands of the ATR-IR spectroscopy listed below with values expressed in reciprocal wave numbers (cm$^{-1}$): 3374; 3272; 2956; 1619; 1556; 1465; 1420; 1394; 1271; 1175; 1015; 975; 836; 766; 751; 741; 730.

The theoretical water content of the hexahydrate of the magnesium salt of valsartan is 19.1%. Using a coupled instrument based on thermogravimetry-Fourier transformation-infrared-spectroscopy (TG-FTIR, IFS 28 from the companies Netzsch Gerätebau GmbH, Selb, Bayern and Bruker Optik GmbH, Karlsruhe), whilst simultaneously measuring the weight loss and identifying the material component given up, using infrared spectroscopy (release of water), the water content was determined for the hexahydrate of the magnesium salt of valsartan $A_{0,Mg}$ with the weight loss up to the plateau for 225° C. a 18.7%. The total formula was calculated for the hexahydrate of the magnesium salt of valsartan $A_{0,Mg}$ from this as $(C_{24}H_{27}N_5O_3)^{2-}Mg^{2+}.5.9H_2O$.

Using thermogravimetry, in a water-free $N_2$ atmosphere, the weight loss, i.e. the water loss for the hexahydrate as a function of temperature, was measured at a heating rate of 10 K·min$^{-1}$. The results for the magnesium salt of valsartan hexahydrate $A_{0,Mg}$ are listed in the following:

| Temperature [° C.] | Weight loss or water loss in % |
|---|---|
| 25 | 0.0 |
| 50 | 1.2 |
| 75 | 4.2 |
| 100 | 11.0 |
| 125 | 16.7 |
| 150 | 17.7 |
| 175 | 18.3 |
| 200 | 18.5 |
| 225 | 18.7 |
| 250 | 18.9 |
| 275 | 19.3 |

Calculation of the interlattice plane intervals from the X-ray powder pattern taken with a Guinier camera is as follows for the characteristic lines for this batch of the magnesium salt of valsartan hexahydrate $A_{0,Mg}$:

d in [Å]: 19.78, 10.13, 9.84, 7.28, 6.00, 5.81, 5.67, 5.21, 5.04, 4.88, 4.21, 4.18, 4.08, 3.95, 3.46, 3.42.

Elementary analysis gives the following measured values of the elements present in the hexahydrate of the magnesium salt of valsartan and of water. The water evaluation is carried out at 130° C. after expulsion. The findings of the elementary analysis, within the error limits, correspond to the sum formula $(C_{24}H_{27}N_5O_3)^{2-}Mg^{2+}.6H_2O$.

| | % found | % calculated |
|---|---|---|
| C | 51.03 | 50.94 |
| H | 7.00 | 6.95 |
| N | 12.45 | 12.38 |
| O | 25.02 | 25.44 |
| Water | 19.08 | 19.10 |
| Mg | 4.35 | 4.29 |

WORKING EXAMPLES

Example 1

Production of the Calcium Salt as the Tetrahydrate $A_{1,Ca}$ In Situ of (S)—N-(1-carboxy-2-methyl-prop-1-yl)-N-pentanoyl-N-[2'-(1H-tetrazol-5-yl)-biphenyl-4-ylmethyl]-amine 30.18 mg of the calcium salt of (S)—N-(1-carboxy-2-methyl-prop-1-yl)-N-pentanoyl-N-[2'-(1H-tetrazol-5-yl)-biphenyl-4-ylmethyl]-amine as tetrahydrate $A_{0,Ca}$ is weighed into a thermobalance TGS-2 (Perkin-Elmer Corp. Norwalk, Conn. USA) and is partially dehydrated at 34° C. in a water-free $N_2$ atmosphere with a flow rate of 50 for a time interval of 50 hours. The observed weight loss, i.e. water loss after the time interval of 50 hours is 7.9%. The water bound at this endpoint for the calcium salt of valsartan was under consideration of the water content for the starting material $A_{0,Ca}$ which is 12.9%, only 5.0%. The consecutive equilibration of the partially dehydrated calcium salt of valsartan is executed in an air atmosphere with a relative humidity of 60% and at a temperature of 23° C. The equilibrated substance obtained is the (S)—N-(1-carboxy-2-methyl-prop-1-yl)-N-pentanoyl-N-[2'-(1H-tetrazol-5-yl)-biphenyl-4-ylmethyl]-amine calcium salt tetrahydrate $A_{1,Ca}$.

The melting point for the tetrahydrate of the calcium salt of valsartan $A_{1,Ca}$ produced according to example 1 for a heating rate of 10 K·min$^{-1}$ and in a closed specimen container with a small internal volume of ca. 22 microliters and a sample weight of 2.67 mg is $T_{fus}$=190° C. The enthalpy of fusion for $A_{1,Ca}$ is calculated from the same measurement as explained above with $\Delta_{fus}H$=79 kJ·mol$^{-1}$.

The infrared spectrum of the (S)—N-(1-carboxy-2-methyl-prop-1-yl)-N-pentanoyl-N-[2'-(1H-tetrazol-5-yl)-biphenyl-4-ylmethyl]-amine calcium salt tetrahydrate $A_{1,Ca}$ is measured with a ATR-IR instrument BX from Perkin Elmer Corp., Beaconsfield, Bucks, England.

The characteristic absorption bands of the ATR-IR spectroscopy listed in the following for the tetrahydrate of the calcium salt of valsartan $A_{1,Ca}$ with values expressed in reciprocal wave numbers (cm$^{-1}$): 3594; 3307; 2960; 1621; 1578; 1459; 1442; 1417; 1407; 1364; 1357; 1319; 1274; 1211; 1180; 1137; 1105; 1099; 1012; 1003; 758; 738; 698.

The water content is in theory 13.2% for a tetrahydrate of the calcium salt of valsartan. Using a thermobalance TGS-2 the water content was determined for the substance produced according to example 1 with 13.4%. An amount of 1.1% $H_2O$ is free and not bound water in the calcium salt of valsartan $A_{1,Ca}$, so the total amount of bound water is 12.3%. A total formula was calculated from this value for $A_{1,Ca}$ as $(C_{24}H_{27}N_5O_3)^{2-}Ca^{2+}\cdot 3.7H_2O$.

Using thermogravimetry, in a water-free $N_2$ atmosphere, the weight loss, i.e. the water loss for the tetrahydrate of the calcium salt of valsartan as a function of temperature, was measured at a heating rate of 10 K·min$^{-1}$. The results for the calcium salt of valsartan tetrahydrate $A_{1,Ca}$ are listed as follows:

| Temperature [° C.] | weight loss or water loss in % |
|---|---|
| 25 | 1.1 |
| 50 | 3.3 |
| 75 | 5.1 |
| 100 | 9.6 |
| 125 | 12.1 |
| 150 | 12.9 |
| 175 | 13.2 |
| 200 | 13.3 |
| 225 | 13.4 |
| 250 | 13.3 |
| 275 | 13.7 |

Example 2

Production of the Calcium Salt as the Tetrahydrate $A_{2,Ca}$ In Situ of (S)—N-(1-carboxy-2-methyl-prop-1-yl)-N-pentanoyl-N-[2'-(1H-tetrazol-5-yl)-biphenyl-4-ylmethyl]-amine 32.17 mg of the calcium salt of (S)—N-(1-carboxy-2-methyl-prop-1-yl)-N-pentanoyl-N-[2'-(1H-tetrazol-5-yl)biphenyl-4-ylmethyl]-amine as tetrahydrate $A_{0,Ca}$ is weighed into a thermobalance TGS-2 (Perkin-Elmer Corp. Norwalk, Conn. USA) and is partially dehydrated at 50° C. in a water-free $N_2$ atmosphere with a flow rate of 50 for a time interval of 21 hours. The weight loss, i.e. water loss is observed directly and reached a value of 9.9%. The water bound at this endpoint for the calcium salt of valsartan is under consideration of the water content for the starting material $A_{0,Ca}$ which is 12.9%, only 3%, a value which corresponds with a calcium salt of valsartan monohydrate.

The equilibration of this monohydrate of the calcium salt of valsartan in an air atmosphere with a relative humidity in air of 29% and at a temperature of 23° C. is directly observed over a time interval of 46 hours in the thermobalance by a practically equilibrium situation with an uptake of 6.0% $H_2O$. The final content of bound water is 9.0%, corresponding to 2.6 mole water per molecule of calcium salt of valsartan. The substance, namely the $(C_{24}H_{27}N_5O_3)^{2-}Ca^{2+}\cdot 2.6H_2O$ is additionally water equilibrated in an exsiccator with a relative humidity of 90.5%, at a temperature of 23° C. and over a time interval of 72 hours. (S)—N-(1-carboxy-2-methyl-prop-1-yl)-N-pentanoyl-N-[2'-(1H-tetrazol-5-yl)-biphenyl-4-ylmethyl]-amine calcium salt tetrahydrate $A_{0,Ca}$ is obtained.

The melting point for the tetrahydrate of the calcium salt of valsartan $A_{2,Ca}$ produced according to example 2, for a heating rate of 10 K·min$^{-1}$ and in a closed specimen container with a small internal volume, and with a sample weight of 1.56 mg measured in a DSC Pyris 1 (Differential Scanning calorimeter) is determined as $T_{fus}$=195° C. and the melting as $\Delta_{fus}H$=89 kJ·mol$^{-1}$.

The water content is in theory 13.2% for a tetrahydrate of the calcium salt of valsartan. Using a thermobalance TGS-2 (Perkin-Elmer Corp. Norwalk, Conn. USA) with a measurement in a water-free $N_2$ atmosphere, the water content for the substance produced according to example 2 for the temperature interval of 25 to 225° C. is determined as 12.6%. A total formula is calculated from this value for $A_{2,Ca}$ as $(C_{24}H_{27}N_5O_3)^{2-}Ca^{2+}\cdot 3.8H_2O$.

Using thermogravimetry, in a water-free $N_2$ atmosphere, the weight loss, i.e. the water loss for the tetrahydrate $A_{2,Ca}$ as a function of temperature, is measured at a heating rate of 10 K·min$^{-1}$. The results are listed as follows:

| Temperature [° C.] | weight loss or water loss in % |
| --- | --- |
| 25 | 0 |
| 50 | 0 |
| 75 | 0 |
| 100 | 4.7 |
| 125 | 11.1 |
| 150 | 11.9 |
| 175 | 12.3 |
| 200 | 12.5 |
| 225 | 12.6 |
| 250 | 12.7 |
| 275 | 13.3 |

Calculation of the interlattice plane intervals from the X-ray powder pattern measured with a Guinier camera is as follows for the characteristic lines for this batch of tetrahydrate of the calcium salt of valsartan $A_{2,Ca}$:

d in [Å]: 16.16, 9.90, 9.40, 8.05, 7.72, 7.04, 6.49, 6.35, 5.82, 4.94, 4.73, 4.13, 3.93.

Example 3

Production of the Calcium Salt as the Trihydrate $B_{1,Ca}$ In Situ of (S)—N-(1-carboxy-2-methyl-prop-1-yl)-N-pentanoyl-N-[2'-(1H-tetrazol-5-yl)-biphenyl-4-ylmethyl]-amine 28.24 mg calcium salt of (S)—N-(1-carboxy-2-methyl-prop-1-yl)-N-pentanoyl-N-[2'-(1H-tetrazol-5-yl)-biphenyl-4-ylmethyl]-amine as tetrahydrate $A_{0,Ca}$ is placed into an open pan of a thermobalance TGS-2 (Perkin-Elmer Corp. Norwalk, Conn. USA) and has been partially dehydrated at 50° C. in a water-free $N_2$ atmosphere having a flow rate of 50 ml·min$^{-1}$ for a time interval of 28 hours. The weight loss, i.e. water loss is observed directly with the thermobalance and the final stage of dehydration is selected at a water loss of 10.0%. The water bound at this endpoint for the product calcium salt of valsartan was 2.9%, a value which corresponds with 0.8 mole water which is in relation with one mole of calcium salt of valsartan.

The equilibration of this monohydrate is spontaneous at a temperature of 22° C. and a relative humidity in air of 34% with a relaxation time of about 1 hour. The final equilibration is practically reached after 9 hours with a content of water of 9.7%. The dehydration-hydration process provided the substance (S)—N-(1-carboxy-2-methyl-prop-1-yl)-N-pentanoyl-N-[2'-(1H-tetrazol-5-yl)-biphenyl-4-ylmethyl]-amine calcium salt trihydrate $B_{1,Ca}$.

The melting point for the trihydrate of the calcium salt of valsartan $B_{1,Ca}$ produced according to example 2, for a heating rate of 10 K·min$^{-1}$ and in a closed specimen container with a small internal volume, and with a sample weight of 3.98 mg is determined as $T_{fus}$=176° C. and the melting enthalpy is $\Delta_{fus}H$=7 kJ·mol$^{-1}$. The crystallinity of the calcium salt of valsartan $B_{1,Ca}$ is ca. 10%.

The water content is determined with a thermobalance TGS-2 (Perkin-Elmer Corp. Norwalk, Conn. USA) with a measurement in a water-free $N_2$ atmosphere and a heating rate of 10 K·min$^{-1}$. The water content for the substance $B_{1,Ca}$, produced according to example 3, is for the plateau at the temperature of 225° C. determined with 9.7%. The total amount of water bound in $B_{1,Ca}$ is 9.2% calculated from the weight loss at 225° C. and the amount of water which is evaporated at 25° C. A total formula is calculated from this value for $B_{1,Ca}$ as $(C_{24}H_{27}N_5O_3)^{2-}Ca^{2+}\cdot 2.7H_2O$.

Using thermogravimetry, in a water-free $N_2$ atmosphere, the weight loss, i.e. the water loss for the trihydrate $B_{1,Ca}$ as a function of temperature, was measured at a heating rate of 10 K·min$^{-1}$. The measurements are elucidated as follows:

| Temperature [° C.] | weight loss or water loss in % |
| --- | --- |
| 25 | 0.5 |
| 50 | 2.0 |
| 75 | 3.9 |
| 100 | 5.7 |
| 125 | 8.1 |
| 150 | 9.2 |
| 175 | 9.5 |
| 200 | 9.7 |
| 225 | 9.7 |
| 250 | 9.9 |
| 275 | 10.2 |

Calculated values of the interlattice plane intervals from the X-ray powder pattern measured with powder diffractometer PW 1710 from Philips Analytical X-ray, 7602 Amelo, NL are corrected with reference measurements made with the Guinier camera (FR 552 from Enraf Nonius, Delft, NL). The corrections for the interlattice plane intervals to reach the values measured and calculated for the Guinier camera from the powder diffractometer PW 1710 were ranging from +0.55 Å for a d value of 16 Å to +0.02 Å for a d value of 5.7 Å. No corrections are necessary for lower d values.

The interlattice plane intervals are given in the following for the trihydrate of the calcium salt of valsartan $B_{1,Ca}$, produced according to example 3:

d in [Å]: 16.1, 11.5, 10.0, 9.42, 9.12, 8.10, 7.78, 7.03, 6.48, 6.08, 5.76, 5.12, 4.91, 4.72, 4.48, 4.31.

Example 4

Production of the Calcium Salt as the Trihydrate $B_{2,Ca}$ In Situ of (S)—N-(1-carboxy-2-methyl-prop-1-yl)-N-pentanoyl-N-[2'-(1H-tetrazol-5-yl)-biphenyl-4-ylmethyl]-amine 33.84 mg calcium salt of (S)—N-(1-carboxy-2-methyl-prop-1-yl)-N-pentanoyl-N-[2'-(1H-tetrazol-5-yl)-biphenyl-4-ylmethyl]-amine as tetrahydrate $A_{0,Ca}$ is placed into an open pan of a thermobalance TGS-2 (Perkin-Elmer Corp. Norwalk, Conn. USA) and the tetrahydrate $A_{0,Ca}$ is been partially dehydrated at 61° C. in a water-free $N_2$ atmosphere with a gas flow of 50 ml·min$^{-1}$ over a time interval of 205 minutes. The weight loss, i.e. water loss is observed directly with the thermobalance and the final stage of dehydration is selected to a water loss of 6.4%. The water still bound at this endpoint for the substance of calcium salt of valsartan was 6.5%, a value which corresponds with 1.9 mole water in relation with one mole of calcium salt of valsartan. The equilibration of the dihydrate at 23° C. and 22% relative humidity in air with a relaxation time of about 30 minutes revealed a production of a trihydrate. The dehydration-rehydration process provided the substance (S)—N-(1-carboxy-2-methyl-prop-1-yl)-N-pentanoyl-N-[2'-(1H-tetrazol-5-yl)-biphenyl-4-ylmethyl]-amine calcium salt trihydrate $B_{2,Ca}$.

The melting point for the trihydrate of the calcium salt of valsartan $B_{2,Ca}$ produced according to example 4, for a heating rate of 10 K·min$^{-1}$, in a closed specimen container with a small internal volume, and with a sample weight of 2.49 mg is determined as $T_{fus}$=198° C. and for the second component $T_{fus}$=204° C. The two melting points are elucidated easily, namely, that the produced material is a mixture of the trihydrate $B_{2,Ca}$ and the tetrahydrate $A_{0,Ca}$. The enthalpy of fusion for the two melting peaks reveal the values for the trihydrate $B_{2,Ca}$ of $\Delta_{fus}H=53$ kJ·mol$^{-1}$ and for the tetrahydrate $A_{0,Ca}$ of $\Delta_{fus}H=4$ kJ·mol$^{-1}$.

The DSC (Differential Scanning calorimetry) curve with a sample weight of 2.49 mg of the trihydrate $B_{2,Ca}$ calcium salt of (S)—N-(1-carboxy-2-methyl-prop-1-yl)-N-pentanoyl-N-[2'-(1H-tetrazol-5-yl)-biphenyl-4-ylmethyl]-amine with a heating rate of 10 K·min$^{-1}$ in an closed specimen container with a small internal volume reveals in addition to the melting peaks at 198 and 204° C. a glass transition as a solid state phenomena related to amorphous substances. The glass transition temperature is determined with a value of $T_g=66°$ C. and the change of the specific heat is for this temperature $\Delta c_p=0.10$ J·(g·K)$^{-1}$. The glass transition temperature observed is an absolute evidence of amorphous material present in the substance produced according to example 4 and the value for the change of the specific heat is a parameter for the quantization of the amorphicity.

An additional amount of estimated 18% is amorphous material, the trihydrate $B_{2,Ca}$ is approximated with the enthalpy of fusion of 53 kJ·mol$^{-1}$ as 78% and the tetrahydrate $A_{0,Ca}$ which has in pure form as starting material the enthalpy of fusion $A_{fus}H=92$ kJ·mol$^{-1}$ is approximated in the produced material of example 4 kJ·mol$^{-1}$ with 4%.

The water content is determined with a thermobalance TGS-2 (Perkin-Elmer Corp. Norwalk, Conn. USA) with a measurement in a water-free N$_2$ atmosphere and a heating rate of 10 K·min$^{-1}$. The water content for the substance $B_{2,Ca}$, produced according to example 4, is for the plateau of the weight loss at the temperature of 225° C. determined with 9.7%. A total formula was calculated from this value for $B_{2,Ca}$ as $(C_{24}H_{27}N_5O_3)^{2-}Ca^{2+}\cdot 2.8H_2O$.

Using thermogravimetry, in a water-free N$_2$ atmosphere, the weight loss, i.e. the water loss for the trihydrate $B_{2,Ca}$ as a function of temperature, is measured at a heating rate of 10 K·min$^{-1}$. The measurements are elucidated as follows:

| Temperature [° C.] | Weight loss or water loss in % |
|---|---|
| 25 | 0 |
| 50 | 0.7 |
| 75 | 1.9 |
| 100 | 5.5 |
| 125 | 8.4 |
| 150 | 9.2 |
| 175 | 9.5 |
| 200 | 9.7 |
| 225 | 9.7 |
| 250 | 9.8 |
| 275 | 10.1 |

Calculated values of the interlattice plane intervals from the X-ray powder pattern measured with a Guinier camera FR 552 from Euraf Nonius, Delft, NL on a X-ray film in transmission geometry, using Cu-K$\alpha_1$ radiation, are obtained for $B_{2,Ca}$. The interlattice plane intervals are given in the following for the trihydrate of the calcium salt of valsartan $B_{2,Ca}$, produced according to example 4:

d in [Å]: 16.2, 11.47, 9.94, 9.44, 9.01, 8.13, 7.80, 7.05, 6.50, 6.09, 5.79, 4.95, 4.16, 4.74.

The enantiomer purity of the salt hydrate produced according to example 4 is determined by a stereo-specific HPLC method. The stereo-specific separation is achieved by achiral column (Chiral AGP). The enantiomer purity for the trihydrate of the calcium salt of valsartan $B_{2,Ca}$ is determined as ee=99.65.

Example 5

Production of the Calcium Salt as the Trihydrate $B_{3,Ca}$ In Situ of (S)—N-(1-carboxy-2-methyl-prop-1-yl)-N-pentanoyl-N-[2'-(1H-tetrazol-5-yl)-biphenyl-4-ylmethyl]-amine 32.15 mg calcium salt of (S)—N-(1-carboxy-2-methyl-prop-1-yl)-N-pentanoyl-N-[2'-(1H-tetrazol-5-yl)-biphenyl-4-ylmethyl]-amine as tetrahydrate $A_{0,Ca}$ is placed into an open pan of a thermobalance TGS-2 (Perkin-Elmer Corp. Norwalk, Conn. USA) and the tetrahydrate $A_{0,Ca}$ is partially dehydrated at 60° C. in a water-free N$_2$ atmosphere with a gas flow of 50 ml·min$^{-1}$ over a time interval of 255 minutes. The weight loss, i.e. water loss is observed with the thermobalance and the selected final stage of dehydration is 7.0%. The water still bound at this endpoint for the substance of calcium salt of valsartan was 5.9%, a value which corresponds with 1.4 mole water in relation with one mole of calcium salt of valsartan. The rehydration at 23° C. and 30% relative humidity in air is observed with a process of a relaxation time of 30 minutes. The dehydration-rehydration process provided the substance (S)—N-(1-carboxy-2-methyl-prop-1-yl)-N-pentanoyl-N-[2'-(1H-tetrazol-5-yl)-biphenyl-4-ylmethyl]-amine calcium salt trihydrate $B_{3,Ca}$.

The melting point for the trihydrate of the calcium salt of valsartan $B_{3,Ca}$ produced according to example 5, for a heating rate of 10 K·min$^{-1}$, in a closed specimen container with a small internal volume, and with a sample weight of 2.85 mg is determined as $T_{fus}=191°$ C. Additional melting peaks are observed for the material produced according to example 5, namely for 196, 205, and 213° C. The enthalpy of fusion for the different melting peaks are used for an approximation of the quantitative analysis of the material produced according to example 5, namely 87% of the material for the melting point 191° C. as $B_{3,Ca}$, 10% of the material for the melting point 196° C. as $B_{2,Ca}$, 0.5% of the material for the melting point 205° C. as $A_{0,Ca}$, and 3% of the material for the melting point 213° C. as $D_{1,Ca}$. The results reveal clearly a material, produced according to example 5, which is dominated by a main component namely $B_{3,Ca}$.

The water content is determined with a thermobalance TGS-2 (Perkin-Elmer Corp. Norwalk, Conn. USA) with a measurement in a water-free N$_2$ atmosphere and a heating rate of 10 K·min$^{-1}$. The water content for the material with $B_{3,Ca}$ as the main component is for the plateau at the temperature of 225° C. determined with 10.1%. A total formula is calculated from for the bound water content of 9.8% for $B_{3,Ca}$ as $(C_{24}H_{27}N_5O_3)^{2-}Ca^{2+}\cdot 2.9H_2O$.

Using thermogravimetry, in a water-free N$_2$ atmosphere, the weight loss, i.e. the water loss for the material, produced according to example 5, with $B_{3,Ca}$ as the dominating component is measured as a function of temperature at a heating rate of 10 K·min$^{-1}$. The measurements reveal the following results:

| Temperature [° C.] | weight loss or water loss in % |
|---|---|
| 25 | 0.3 |
| 50 | 1.2 |
| 75 | 2.5 |

-continued

| Temperature [° C.] | weight loss or water loss in % |
|---|---|
| 100 | 5.7 |
| 125 | 8.7 |
| 150 | 9.6 |
| 175 | 9.9 |
| 200 | 10.0 |
| 225 | 10.1 |
| 250 | 10.2 |
| 275 | 10.5 |

Calculated values of the interlattice plane intervals from the X-ray powder pattern measured with a Guinier camera FR 552 from Euraf Nonius, Delft, NL on a X-ray film in transmission geometry, using Cu-K$\alpha_1$ radiation, are obtained for the substance produced according to example 5, with the main component $B_{3,Ca}$.

The interlattice plane intervals are given in the following for the material, produced according to example 5, with the trihydrate of the calcium salt of (S)—N-(1-carboxy-2-methyl-prop-1-yl)-N-pentanoyl-N-[2'-(1H-tetrazol-5-yl)-biphenyl-4-ylmethyl]-amine $B_{3,Ca}$ as the dominating component:

d in [Å]: 16.11, 11.44, 9.90, 9.40, 9.01, 8.04, 7.73, 7.03, 6.47, 6.33, 6.09, 5.80, 5.17, 4.95, 4.73, 4.48, 4.33, 415, 4.11, 3.94, 3.61.

The infrared spectrum of the (S)—N-(1-carboxy-2-methyl-prop-1-yl)-N-pentanoyl-N-[2'-(1H-tetrazol-5-yl)-biphenyl-4-ylmethyl]-amine calcium salt trihydrate $B_{3,Ca}$, as the main component of the material produced according to example 5 is measured with a ATR-IR instrument BX from Perkin Elmer Corp., Beaconsfield, Bucks, England. The characteristic absorption bands of the ATR-IR spectroscopy are listed in the following for the material produced according to example 5, containing the dominating substance, namely the calcium salt as trihydrate (S)—N-(1-carboxy-2-methyl-prop-1-yl)-N-pentanoyl-N-[2'-(1H-tetrazol-5-yl)-biphenyl-4-ylmethyl]-amine $B_{3,Ca}$ with values expressed in reciprocal wave numbers (cm$^{-1}$): 3594; 3309; 2959; 2930; 2870; 1621; 1577; 1505; 1458; 1416; 1405; 1354; 1273; 1210; 1179; 1138; 1104; 1099; 1012; 1003; 974; 941; 906; 856; 841; 737; 667.

Example 6

Production of the Calcium Salt as Monohydrate $C_{1,Ca}$ In Situ of (S)—N-(1-carboxy-2-methyl-prop-1-yl)-N-pentanoyl-N-[2'-(1H-tetrazol-5-yl)-biphenyl-4-ylmethyl]-amine 65.5 mg calcium salt of (S)—N-(1-carboxy-2-methyl-prop-1-yl)-N-pentanoyl-N-[2'-(1H-tetrazol-5-yl)-biphenyl-4-ylmethyl]-amine as tetrahydrate $A_{0,Ca}$ is pressed into an open crucible of a device which allows to set a temperature and a humidity program as function of time and register for selected time intervals the X-ray diffraction pattern (powder diffraction chamber X'Pert from Philips Analytical X-ray, 7602 Almelo, NL). The isothermal temperature is 40° C. and the water-free N$_2$ atmosphere is set at a flow rate of 100 ml·min$^{-1}$. In a parallel production step 4.66 mg (S)—N-(1-carboxy-2-methyl-prop-1-yl)-N-pentanoyl-N-[2'-(1H-tetrazol-5-yl)-biphenyl-4-ylmethyl]-amine as tetrahydrate $A_{0,Ca}$ is placed in an open crucible of a thermobalance TGS-2 (Perkin-Elmer Corp., Norwalk, Conn. USA) and the tetrahydrate $A_{0,Ca}$ is exposed to the following conditions: isothermal temperature 40° C., and to a water-free atmosphere with a flow rate of 50 ml·min$^{-1}$. The substance obtained in both of the devices after 66 hours was the monohydrate of the calcium salt of (S)—N-(1-carboxy-2-methyl-prop-1-yl)-N-pentanoyl-N-[2'-(1H-tetrazol-5-yl)-biphenyl-4-ylmethyl]-amine $C_{1,Ca}$.

The water content was determined with the thermobalance TGS-2. The weight loss, i.e. the water loss after 66 hours in the water-free atmosphere was 9.8%, yielding to a water content in the product $C_{1,Ca}$ of 3.1%. A total formula was calculated from this value for $C_{1,Ca}$ produced according to example 7 as $(C_{24}H_{27}N_5O_3)^{2-}Ca^{2+}\cdot0.9H_2O$.

Calculation of the interlattice plane intervals of the monohydrate of the calcium salt of valsartan $C_{1,Ca}$ had been taken from the X-ray powder patterns measured with the powder diffraction chamber X'Pert from Philips Analytical X-ray, 7602 Almelo, NL. The characteristic lines for the product $C_{1,Ca}$ are listed in the following:

d in [Å]: 15.96, 15.04, 11.56, 9.85, 9.40, 8.02, 7.53, 6.11, 4.49.

Example 7

Production of the di-{calcium salt of (S)—N-(1-carboxy-2-methyl-prop-1-yl)-N-pentanoyl-N-[2'-(1H-tetrazol-5-yl)-biphenyl-4-ylmethyl]-amine}pentahydrate $D_{1,Ca}$ In Situ 30.65 mg of the calcium salt as tetrahydrate of (S)—N-(1-carboxy-2-methyl-prop-1-yl)-N-pentanoyl-N-[2'-(1H-tetrazol-5-yl)-biphenyl-4-ylmethyl]-amine $A_{0,Ca}$ is placed into an open pan of a thermobalance TGS-2 (Perkin-Elmer Corp. Norwalk, Conn. USA) and the tetrahydrate $A_{0,Ca}$ is exposed at a temperature of 90° C. in a water-free atmosphere with a gas flow of 50 ml·min$^{-1}$ over a time interval of 55 minutes. The dehydration of the tetrahydrate reached at the selected final stage a weight loss, i.e. a water loss of 9.7%. The water bound at this endpoint for the product of calcium salt of valsartan was 3.2%, a value which corresponds to 0.9 mole water in relation with one mole of calcium salt of valsartan. The hydration process is performed at 23° C. and with a relative humidity in air of 28%. The final equilibration is practically reached after 4 hours. The process provided the product di-{calcium salt of (S)—N-(1-carboxy-2-methyl-prop-1-yl)-N-pentanoyl-N-[2'-(1H-tetrazol-5-yl)-biphenyl-4-ylmethyl]-amine}pentahydrate $D_{1,Ca}$.

The melting point for the di-{calcium salt of (S)—N-(1-carboxy-2-methyl-prop-1-yl)-N-pentanoyl-N-[2'-(1H-tetrazol-5-yl)-biphenyl-4-ylmethyl]-amine}pentahydrate $D_{1,Ca}$ produced according to example 7, for a heating rate of 10 K·min$^{-1}$, in a closed specimen container with a small internal volume, and with a sample weight of 1.41 mg is determined as $T_{fus}=212°$ C. and the melting enthalpy is $\Delta_{fus}H=15$ kJ·Mol$^{-1}$.

The water content is determined with a thermobalance TGS-2 (Perkin-Elmer Corp. Norwalk, Conn. USA) with a measurement in a water-free N$_2$ atmosphere and a heating rate of 10 K·min$^{-1}$. The water content for the substance $D_{1,Ca}$, produced according to example 7, is for the plateau at the temperature of 225° C. determined with 8.1%. A total formula is calculated with the amount of bound water which is 8.0% for $D_{1,Ca}$ as $[(C_{24}H_{27}N_5O_3)^{2-}Ca^{2+}]_2\cdot4.6H_2O$.

Using thermogravimetry, in a water-free N$_2$ atmosphere, the weight loss, i.e. the water loss for the di-{calcium salt of (S)—N-(1-carboxy-2-methyl-prop-1-yl)-N-pentanoyl-N-[2'-(1H-tetrazol-5-yl)-biphenyl-4-ylmethyl]-amine}pentahydrate $D_{1,Ca}$, produced according to example 7, is measured as a function of temperature at a heating rate of 10 K·min$^{-1}$. The measurements reveal the following results:

| Temperature [° C.] | Weight loss or water loss in % |
|---|---|
| 25 | 0.1 |
| 50 | 1.7 |
| 75 | 3.3 |
| 100 | 5.1 |
| 125 | 7.1 |
| 150 | 7.7 |
| 175 | 7.9 |
| 200 | 8.0 |
| 225 | 8.1 |
| 250 | 8.3 |
| 275 | 8.6 |

The infrared spectrum of the di-{calcium salt of (S)—N-(1-carboxy-2-methyl-prop-1-yl)-N-pentanoyl-N-[2'-(1H-tetrazol-5-yl)-biphenyl-4-ylmethyl]-amine}pentahydrate is measured with a ATR-IR instrument BX from Perkin Elmer Corp., Beaconsfield, Bucks, England.

The characteristic absorption bands of the ATR-IR spectroscopy for the di-{calcium salt of (S)—N-(1-carboxy-2-methyl-prop-1-yl)-N-pentanoyl-N-[2'-(1H-tetrazol-5-yl)-biphenyl-4-ylmethyl]-amine}pentahydrate $D_{1,Ca}$ are listed in the following with values expressed in reciprocal wave numbers (cm$^{-1}$): 3329; 2959; 2930; 2870; 1578; 1506; 1459; 1405; 1354; 1302; 1260; 1208; 1176; 1143; 1104; 1012; 1004; 973; 941; 860; 839; 821; 757; 737; 667.

Calculated values of the interlattice plane intervals from X-ray powder patterns were obtained from a Guinier camera FR 552 from Euraf Nonius, Delft, NL on a X-ray film in transmission geometry, using Cu-K$\alpha_1$ radiation.

The characteristic interlattice plane intervals are given in the following for the di-{calcium salt of (S)—N-(1-carboxy-2-methyl-prop-1-yl)-N-pentanoyl-N-[2'-(1H-tetrazol-5-yl)-biphenyl-4-ylmethyl]-amine}pentahydrate $D_{1,Ca}$, produced according to example 7:

d in [Å]: 15.46, 11.45, 9.36, 9.04, 7.75, 6.46, 6.09, 5.82, 5.66, 5.16, 4.76, 4.48, 3.83, 3.60.

Example 8

Production of the Calcium Salt of (S)—N-(1-carboxy-2-methyl-prop-1-yl)-N-pentanoyl-N-[2'-(1H-tetrazol-5-yl)-biphenyl-4-ylmethyl]-amine as Amorphous Substance $E_{1,Ca}$ In Situ 3.53 mg calcium salt of (S)—N-(1-carboxy-2-methyl-prop-1-yl)-N-pentanoyl-N-[2'-(1H-tetrazol-5-yl)-biphenyl-4-ylmethyl]-amine as tetrahydrate $A_{0,Ca}$ is put into a hermetically closed specimen container made from gold with an internal volume of ca. 22 microliters. The starting substance $A_{0,Ca}$ is heated up in a DSC Pyris 1 after cooling to −50° C. to 216° C. and therefore transferred into the molten phase. The substance is taken out of the gold container after cooling the container to room temperature. (S)—N-(1-carboxy-2-methyl-prop-1-yl)-N-pentanoyl-N-[2'-(1H-tetrazol-5-yl)-biphenyl-4-ylmethyl]-amine calcium salt $E_{1,Ca}$ in amorphous form is obtained.

The substance $E_{1,Ca}$, produced according to example 8, contains 12.9% of water.

The thermal characterization of the calcium salt of (S)—N-(1-carboxy-2-methyl-prop-1-yl)-N-pentanoyl-N-[2'-(1H-tetrazol-5-yl)-biphenyl-4-ylmethyl]-amine in amorphous form $E_{1,Ca}$ with a DSC Pyris 1 (Perkin-Elmer, Norwalk, Conn. USA) for a heating rate of 10 K·min$^{-1}$ and in a closed specimen container from gold with a small internal volume, reveals a glass transition temperature $T_g=101°$ C. with a change of the specific heat capacity at the temperature region of the melting point of $\Delta c_p=0.64$ J·(g·K)$^{-1}$. No melting point and no enthalpy of fusion is observed up to a temperature of 216° C. measured with the DSC Pyris 1 under the same conditions as performed for the glass transition measurements.

The infrared spectrum of the amorphous calcium salt of (S)—N-(1-carboxy-2-methyl-prop-1-yl)-N-pentanoyl-N-[2'-(1H-tetrazol-5-yl)-biphenyl-4-ylmethyl]-amine $E_{1,Ca}$ is measured with an ATR-IR instrument BX from Perkin Elmer Corp., Beaconsfield, Bucks, England.

The characteristic absorption bands of the ATR-IR spectroscopy are shown for the amorphous substance $E_{1,Ca}$, produced according to example 8, by the following values expressed in reciprocal wave numbers (cm$^{-1}$): 3587; 3307; 3182; 3053; 2961; 2870; 2358; 1621; 1578; 1506; 1459; 1441; 1417; 1364; 1319; 1301; 1274; 1211; 1180; 1137; 1105; 1099; 1013; 1003; 974; 941; 864; 856; 844; 823; 758; 738; 666.

Example 9

Production of the Calcium Salt of (S)—N-(1-carboxy-2-methyl-prop-1-yl)-N-pentanoyl-N-[2'-(1H-tetrazol-5-yl)-biphenyl-4-ylmethyl]-amine as amorphous substance $F_{1,Ca}$ In Situ 4.14 mg of the substance of the calcium salt trihydrate of (S)—N-(1-carboxy-2-methyl-prop-1-yl)-N-pentanoyl-N-[2'-(1H-tetrazol-5-yl)-biphenyl-4-ylmethyl]-amine $B_{3,Ca}$ is placed in an open crucible of a thermobalance TGS-2 (Perkin-Elmer, Norwalk, Conn. USA) and heated with a heating rate of 10 K·min$^{-1}$ from room temperature up to 225° C. The substance $B_{3,Ca}$ is exposed in the thermobalance to a water-free atmosphere. The dehydrated substance obtained with a weight loss, i.e. water loss of 9.4% at 225° C. is consecutively exposed to 31% relative humidity and 23° C. in air and a rehydration over 18 hours lead to the product, namely the amorphous calcium salt of (S)—N-(1-carboxy-2-methyl-prop-1-yl)-N-pentanoyl-N-[2'-(1H-tetrazol-5-yl)-biphenyl-4-ylmethyl]-amine $F_{1,Ca}$.

The substance $F_{1,Ca}$, produced according to example 9, is characterized with a DSC Pyris 1 (Perkin-Elmer, Norwalk, Conn. USA) applying a heating rate of 10 K·min$^{-1}$ and using a closed specimen container from gold with a small internal volume. The calcium salt of (S)—N-(1-carboxy-2-methyl-prop-1-yl)-N-pentanoyl-N-[2'-(1H-tetrazol-5-yl)-biphenyl-4-ylmethyl]-amine as amorphous substance $F_{1,Ca}$ allowed to elucidate the observed glass transition with the DSC (Differential Scanning calorimeter). The glass transition temperature is $T_g=139°$ C. and the change of the specific heat capacity at the temperature region of the glass transition is $\Delta c_p=0.42$ J·(g·K)$^{-1}$. No melting point and no enthalpy of fusion is observed in the DSC when the substance $F_{1,Ca}$ is after cooling to −50° C. heated up to 220° C. with a heating rate of 10 K·min$^{-1}$. Therefore, the substance $F_{1,Ca}$ has a crystallinity which is not detectable with the method applied and the crystallinity is by an estimation of the sensitivity of the DSC Pyris 1 below 1%. The combined thermodynamic data existing, namely melting point and enthalpy of fusion are an absolute prerequisite of a crystalline material or a crystalline substance.

The water content of the amorphous calcium salt of (S)—N-(1-carboxy-2-methyl-prop-1-yl)-N-pentanoyl-N-[2'-(1H-tetrazol-5-yl)-biphenyl-4-ylmethyl]-amine $F_{1,Ca}$ is determined using thermogravimetry, in a water-free atmosphere. The weight loss, i.e. the water loss for the substance $F_{1,Ca}$ as a function of temperature, is measured at a heating rate of 10 K·min$^{-1}$ and the results are listed in the following.

| Temperature [° C.] | Weight loss or water loss in % |
|---|---|
| 25 | 0.6 |
| 50 | 3.0 |
| 75 | 5.6 |
| 100 | 7.1 |
| 125 | 7.9 |
| 150 | 8.3 |
| 175 | 8.6 |
| 200 | 8.6 |
| 225 | 8.8 |

The total formula of $F_{1,Ca}$ is calculated as $(C_{24}H_{27}N_5O_3)^{2-}Ca^{2+}$ containing 8.8% water.

Example 10

Production of the Magnesium Salt as Hexahydrate $A_{1,Mg}$ In Situ of (S)—N-(1-carboxy-2-methyl-prop-1-yl)-N-pentanoyl-N-[2'-(1H-tetrazol-5-yl)-biphenyl-4-ylmethyl]-amine 28.81 mg of the magnesium salt of (S)—N-(1-carboxy-2-methyl-prop-1-yl)-N-pentanoyl-N-[2'-(1H-tetrazol-5-yl)-biphenyl-4-ylmethyl]-amine as hexahydrate $A_{0,Mg}$ is placed into an open crucible of a thermobalance TGS-2 (Perkin-Elmer, Norwalk, Conn. USA) and treated in a water-free $N_2$ atmosphere at a temperature of 50° C., having a flow rate of 50 ml·min$^{-1}$ for a time interval of 200 minutes. The weight loss, i.e. water loss at the endpoint was 9.4%. The water still bound at this end point for the magnesium salt of valsartan was under consideration of the water content for the start material $A_{0,Mg}$ which is 18.7%, corresponds to 2.6 mole of water in relation with one molecule magnesium salt of valsartan. The substance obtained after this dehydration step is practically a trihydrate, which is exposed in a consecutive step in air to a relative humidity of 31% at 24° C. The uptake of water revealed a relaxation time of about 70 minutes. The substance obtained in reaching an equilibrium condition is the polymorph $A_{1,Mg}$ hexahydrate of the magnesium salt of (S)—N-(1-carboxy-2-methyl-prop-1-yl)-N-pentanoyl-N-[2'-(1H-tetrazol-5-yl)-biphenyl-4-ylmethyl]-amine.

The melting point for hexahydrate of the magnesium salt of (S)—N-(1-carboxy-2-methyl-prop-1-yl)-N-pentanoyl-N-[2'-(1H-tetrazol-5-yl)-biphenyl-4-ylmethyl]-amine $A_{1,Mg}$, produced according to example 10, for a heating rate of 10 K·min$^{-1}$, and measured in a closed specimen container with a small volume of ca. 22 microliters, and with a sample weight of 1.92 mg is $T_{fus}=134°$ C. The enthalpy of fusion measured also with a DSC Pyris 1 is for $A_{1,Mg}$, produced according to example 10, $\Delta_{fus}H=46$ kJ·Mol$^{-1}$.

The water content is in theory 19.1% for the hexahydrate of the magnesium salt of valsartan. The water content of the hexahydrate of the magnesium salt of valsartan of the polymorph $A_{1,Mg}$ is 17.4%, measured as weight loss for the plateau at 225° C. The total formula calculated from this as the polymorph of the hexahydrate $A_{1,Mg}$ is $(C_{24}H_{27}N_5O_3)^{2-}Mg^{2+}$ ·5.5H$_2$O.

Using thermogravimetry, in a water-free $N_2$ atmosphere, the weight loss, i.e. the water loss for the polymorph of the hexahydrate $A_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine produced according to example 7, is as a function of temperature, measured at a heating rate of 10 K·min$^{-1}$ as follows:

| Temperature [° C.] | Weight loss or water loss in % |
|---|---|
| 25 | 0 |
| 50 | 0.9 |
| 75 | 6.8 |
| 100 | 14.3 |
| 125 | 15.7 |
| 150 | 16.5 |
| 175 | 17.0 |
| 200 | 17.2 |
| 225 | 17.4 |
| 250 | 17.8 |
| 275 | 18.3 |

The solid state characterization of the magnesium salt of (S)—N-(1-carboxy-2-methyl-prop-1-yl)-N-pentanoyl-N-[2'-(1H-tetrazol-5-yl)-biphenyl-4-ylmethyl]-amine for the polymorph of the hexahydrate $A_{1,Mg}$ is achieved by a X-ray powder pattern and by the evaluation of the reflections into the interlattice plane intervals. The measurements are made with a Guinier camera and the calculated lines for $A_{1,Mg}$, namely the polymorph of the hexahydrate of the magnesium salt of (S)—N-(1-carboxy-2-methyl-prop-1-yl)-N-pentanoyl-N-[2'-(1H-tetrazol-5-yl)-biphenyl-4-ylmethyl]-amine are expressed in interlattice plane intervals as follows:

d in [Å]: 19.58, 16.63, 10.30, 9.83, 7.40, 6.83, 6.01, 5.93, 5.52, 5.34, 5.20, 5.11, 5.02, 4.87, 4.51, 4.13, 4.06, 3.95, 3.73, 3.63, 3.42.

The enantiomer purity of the salt hydrate produced according to example 10, namely $A_{1,Mg}$ is determined by a stereospecific HPLC method. The enantiomer purity is determined as ee=99.63%.

Example 11

Production of a material as mixture of the magnesium salt of (S)—N-(1-carboxy-2-methyl-prop-1-yl)-N-pentanoyl-N-[2'-(1H-tetrazol-5-yl)-biphenyl-4-ylmethyl]-amine as tetrahydrate $B_{1,Mg}$ and the amorphous substance $E_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine and the crystalline substance as monohydrate $D_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine.

71.4 mg of magnesium salt of (S)—N-(1-carboxy-2-methyl-prop-1-yl)-N-pentanoyl-N-[2'-(1H-tetrazol-5-yl)-biphenyl-4-ylmethyl]-amine as hexahydrate $A_{0,Mg}$ is brought into an open crucible of a device which allows to set a temperature and a humidity program as function of time and register for selected time intervals the X-ray diffraction pattern (powder diffraction chamber X'Pert from Philips Analytical X-ray, 7602 Almelo, NL). The isothermal temperature is set at 35° C. and the water-free $N_2$ atmosphere is achieved with a flow rate of 100 ml·min$^{-1}$. In a parallel production step 5.36 mg magnesium salt of valsartan as hexahydrate $A_{0,Mg}$ is filled into an open crucible of a thermobalance TGS-2 (Perkin-Elmer Corp. Norwalk, Conn. USA) and the start material was exposed to practically identical conditions as the start material in the X-ray device, namely an isothermal temperature of 35° C. and a water-free atmosphere with a flow rate 50 ml·min$^{-1}$. The substance obtained after 42 hours in the thermobalance is the monohydrate $D_{1,Mg}$ of the magnesium salt of (S)—N-(1-carboxy-2-methyl-prop-1-yl)-N-pentanoyl-N-

[2'-(1H-tetrazol-5-yl)-biphenyl-4-ylmethyl]-amine. The substance obtained in the powder diffraction chamber X'Pert is determined by the interlattice plane intervals as monohydrate $D_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine.

The bound water content of the monohydrate $D_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine produced according to example 11 is determined with the thermobalance TGS-2 and is 2.8%. The total formula for $D_{1,Mg}$ is calculated from this as $(C_{24}H_{27}N_5O_3)^{2-}Mg^{2+} \cdot 0.74H_2O$.

Calculation of the interlattice plane intervals from the X-ray powder pattern taken with temperature-humidity powder diffraction chamber X'Pert is for the most important lines of the monohydrate $D_{1,Mg}$ of the magnesium valsartan:

d in [Å]: 15.10, 10.87, 10.27, 7.66, 7.21, 5.12, 4.75.

The substance, namely the monohydrate $D_{1,Mg}$ is kept for additional 35 hours at 35° C. in a water-free atmosphere in the thermobalance as well as in the powder diffraction chamber X'Pert. Both of the substances obtained after 70 hours from the beginning of the treatment in the two different devices revealed according to the thermobalance and the X-ray diffraction pattern the existence of the monohydrate $D_{1,Mg}$ of the magnesium salt of valsartan. After 70 hours both of the substances were exposed to a higher relative humidity. In the X-ray device X'Pert the conditions were 26° C. and the relative humidity 45%. In the thermobalance the conditions were 23° C. and 30% relative humidity in air. Both of the materials obtained, produced according to example 11 are mixtures of the tetrahydrate $B_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine and the amorphous magnesium salt of (S)—N-(1-carboxy-2-methyl-prop-1-yl)-N-pentanoyl-N-[2'-(1H-tetrazol-5-yl)-biphenyl-4-ylmethyl]-amine $E_{1,Mg}$.

The solid state characterization of the material produced finally after equilibration according to example 11 is performed with a DSC Pyris 1 from Perkin-Elmer Corp., Norwalk, Conn. USA. The glass transition is measured with a sample weight of 2.57 mg in a sealed gold container with a small internal volume of ca. 22 microliters and applying a heating rate of 10 K·min$^{-1}$. The glass transition temperature for the amorphous magnesium salt of valsartan $E_{1,Mg}$ as a part of the material produced according to example 11 is $T_g=100°$ C. and the change of the specific heat $\Delta c_p=0.3$ J·(g·K)$^{-1}$.

The water content of the material produced according to the example 11 within the powder diffraction chamber X'Pert is for the magnesium salt of (S)—N-(1-carboxy-2-methyl-prop-1-yl)-N-pentanoyl-N-[2'-(1H-tetrazol-5-yl)-biphenyl-4-ylmethyl]-amine 13.0% measured with a thermobalance TGS-2. The total formula is approximated from this content of water for the crystalline part $B_{1,Mg}$ of the material produced according to example 11 as $(C_{24}H_{27}N_5O_3)^{2-}Mg^{2+} \cdot 3.8H_2O$.

The material, produced according to example 11 within the powder diffraction chamber X'Pert with the main component $E_{1,Mg}$ and the second component $B_{1,Mg}$ shows the following loss of water as a function of temperature measured with a thermobalance TGS-2 (Perkin-Elmer Corp. Norwalk, Conn. USA). The heating rate selected was 10 K·min$^{-1}$. The weight loss is tabulated as follows:

| Temperature [° C.] | weight loss or water loss in % |
| --- | --- |
| 25 | 0 |
| 50 | 2.1 |
| 75 | 6.3 |
| 100 | 9.4 |
| 125 | 11.1 |
| 150 | 12.0 |
| 175 | 12.3 |
| 200 | 12.6 |
| 225 | 13.0 |
| 250 | 13.5 |
| 275 | 14.2 |

The crystalline part $B_{1,Mg}$ as the tetrahydrate of the magnesium salt of valsartan has been characterized with calculated plane intervals from X-ray measurements performed with a temperature-humidity powder diffraction chamber. The characteristic lines for the crystalline part of this material are listed as follows:

d in [Å]: 15.82, 11.02, 8.03.

Measurements of the infrared spectrum took place by means of ATR-IR (Attenuated Total Reflection-Infrared Spectroscopy) using the instrument BX. The following characteristic absorption bands expressed in reciprocal wave numbers (cm$^{-1}$) for the material produced according to example 11 within the thermobalance TGS-2 of Perkin-Elmer Corp., namely the amorphous from $E_{1,Mg}$ as the main component and the crystalline form $B_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine:

3182; 2960; 2870; 1596; 1508; 1460; 1406; 1359; 1302; 1264; 1206; 1174; 1104; 1013; 1005; 975; 941; 845; 819; 785; 738; 666.

Example 12

Production of the Trihydrate $C_{1,Mg}$ of the Magnesium Salt of (S)—N-(1-carboxy-2-methyl-prop-1-yl)-N-pentanoyl-N-[2'-(1H-tetrazol-5-yl)-biphenyl-4-ylmethyl]-amine 76.3 mg of magnesium salt of (S)—N-(1-carboxy-2-methyl-prop-1-yl)-N-pentanoyl-N-[2'-(1H-tetrazol-5-yl)-biphenyl-4-ylmethyl]-amine as hexahydrate $A_{0,Mg}$ is pressed into an open crucible of a device which allows to set a temperature and a humidity program as function of time and register for selected time intervals the X-ray diffraction pattern (powder diffraction chamber X'Pert). The isothermal temperature is 28° C. and the water-free N$_2$ atmosphere is set at a flow rate of 100 ml·min$^{-1}$. In a parallel production step 4.75 mg of magnesium salt of valsartan as hexahydrate $A_{0,Mg}$ is placed in an open crucible of a thermobalance TGS-2. The atmosphere in the thermobalance is water-free and the instrument is flashed with a N$_2$ flow of 50 ml·min$^{-1}$. The substance obtained after 13 hours is the trihydrate $C_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine.

The water content of the substance $C_{1,Mg}$ is determined with a thermobalance TGS-2. The weight loss, i.e. water loss after 13 hours in a water-free atmosphere at a temperature of 28° C. is 8.5%, yielding a bound water content in the product $C_{1,Mg}$ of 10.0%. A total formula is calculated from this value for $C_{1,Mg}$ as $(C_{24}H_{27}N_5O_3)^{2-}Mg^{2+} \cdot 2.8H_2O$.

Calculation of the interlattice plane intervals is taken from X-ray powder patterns measured with a powder diffraction chamber X'Pert. The characteristic lines for the trihydrate $C_{1,Mg}$ of the magnesium salt of valsartan are as follows:

d in [Å]: 17.94, 10.23, 8.96, 7.18, 6.97, 6.81, 6.24, 5.93, 5.84, 5.72, 5.59, 5.42, 5.25, 5.11, 5.01, 4.82, 4.67, 4.57, 4.49, 4.30, 4.19, 4.13, 4.02, 3.88.

Example 13

Production of the Magnesium Salt of (S)—N-(1-carboxy-2-methyl-prop-1-yl)-N-pentanoyl-N-[2'-(1H-tetrazol-5-yl)-biphenyl-4-ylmethyl]-amine in Amorphous Form $E_{1,Mg}$ 4.02 mg magnesium salt of (S)—N-(1-carboxy-2-methyl-prop-1-yl)-N-pentanoyl-N-[2'-(1H-tetrazol-5-yl)-biphenyl-4-ylmethyl]-amine as hexahydrate $A_{0,Mg}$ is filled into a sample pan of a DSC Pyris 1 and the substance was cooled to −50° C. and heated up to 145° C. The cooling rate was 100 K·min$^{-1}$ and heating was 10 K·min$^{-1}$. After cooling the molten substance to room temperature the substance $E_{1,Mg}$ was obtained as amorphous form of the magnesium salt of (S)—N-(1-carboxy-2-methyl-prop-1-yl)-N-pentanoyl-N-[2'-(1H-tetrazol-5-yl)-biphenyl-4-ylmethyl]-amine.

The characterization of the substance $E_{1,Mg}$, produced according to example 14 is performed with the DSC Pyris 1. The cooling of the obtained substance $E_{1,Mg}$ to −50° C. and the heating up to 145° C. in a DSC Pyris 1 with a heating rate of 10 K·min$^{-1}$ in a sealed gold container with a small internal volume revealed a glass transition phenomena. The glass transition temperature measured for the amorphous form $E_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine is $T_g$=73° C. and the change of the specific heat capacity is $\Delta c_p$=0.53 J·(g·K)$^{-1}$.

The water content is measured in a water-free $N_2$ atmosphere and at a heating rate of 10 K·min$^{-1}$ using a thermobalance TGS-2. The sample weight is 2.5 mg and the water content is determined for the amorphous form $E_{1,Mg}$ of the magnesium salt of (S)—N-(1-carboxy-2-methyl-prop-1-yl)-N-pentanoyl-N-[2'-(1H-tetrazol-5-yl)-biphenyl-4-ylmethyl]-amine, produced according to example 13 at the plateau of the weight loss for a temperature of 225° C. with 15.5%. The total formula of $E_{1,Mg}$ was calculated as $(C_{24}H_{27}N_5O_3)^{2-}Mg^{2+}$ containing 15.5% water.

Measurements of the infrared spectrum took place by means of ATR-IR (Attenuated Total Reflexion-Infrared Spectroscopy) using an instrument BX. The following most important absorption bands expressed in reciprocal wave numbers (cm$^{-1}$) characterize the magnesium salt of (S)—N-(1-carboxy-2-methyl-prop-1-yl)-N-pentanoyl-N-[2'-(1H-tetrazol-5-yl)-biphenyl-4-ylmethyl]-amine in amorphous form $E_{1,Mg}$ produced according to example 13:

3189; 2959; 2871; 2356; 1589; 1507; 1459; 1405; 1358; 1299; 1263; 1206; 1174; 1104; 1013; 1005; 974; 942; 841; 736; 668.

Formulation Example 1

Directly Compressed Tablet

| No. | Ingredient | proportion per batch [g] | proportion per tablet core [mg] |
|---|---|---|---|
| 1 | valsartan calcium salt tetrahydrate according to the present invention | 134.24 | 80 |
| 2 | Avicel PH 102 (microcrystalline cellulose) | 60.408 | 36 |
| 3 | lactose (crystalline) | 96.1494 | 57.3 |
| 4 | crospovidone | 7.551 | 4.5 |
| 5 | aerosil 200 (silica, colloidal anhydrous) | 0.839 | 0.5 |
| 6 | magnesium stearate (vegetable) | 6.2086 | 3.7 |

Ingredient no. 1 is sieved through a 0.5 mm sieve and mixed for 15 minutes in a Turbula with ingredients 1-6. Tablets are compress using a single punch tablet press with punches of a diameter of 8 mm.

Formulation Example 2

Tablet Produced by Roller Compaction

| No. | Ingredient | proportion per batch [g] | proportion per tablet core [mg] |
|---|---|---|---|
| 1 | valsartan magnesium salt hexahydrate according to the present invention | 400 | 80 |
| 2 | Avicel PH 102 (microcrystalline cellulose) | 270 | 54 |
| 3 | crospovidone | 75 | 15 |
| 4 | aerosil 200 (silica, colloidal anhydrous) | 7.5 | 1.5 |
| 5 | magnesium stearate | 15 | 3 |
| 6 | magnesium stearate | 7.5 | 1.5 |

Ingredients no. 1-5 are mixed for 50 minutes and compacted on a Freund roller compactor. The band is milled and after admixing ingredient no 6, compressed into tablets using a single punch tablet press with punches of a diameter of 8 mm.

What is claimed is:

1. An amorphous magnesium salt of valsartan characterized by
   (i) a water content of 16±3%
   (ii) a glass transition of 78±20° C.
   (iii) no melting point
   (iv) no enthalpy of fusion.

* * * * *